(12) United States Patent
Dadachanji

(10) Patent No.: US 11,633,543 B2
(45) Date of Patent: Apr. 25, 2023

(54) DEVICE FOR LOCKING A PLUNGER ROD OF A SYRINGE AFTER USE AND PREVENTING RE-USE OF THE SYRINGE, AND SYRINGE ASSEMBLY

(71) Applicant: KAISHA PACKAGING Private Ltd., Mumbai (IN)

(72) Inventor: Rishad Kairus Dadachanji, Mumbai (IN)

(73) Assignee: KAISHA PACKAGING PRIVATE LIMITED, Maharashtra (IN)

( * ) Notice: Subject to any disclaimer, the term of this patent is extended or adjusted under 35 U.S.C. 154(b) by 368 days.

(21) Appl. No.: 17/025,116

(22) Filed: Sep. 18, 2020

(65) Prior Publication Data

US 2021/0077738 A1    Mar. 18, 2021

(30) Foreign Application Priority Data

Sep. 18, 2019  (EP) .................................... 19198135

(51) Int. Cl.
  *A61M 5/315*  (2006.01)
  *A61M 5/31*   (2006.01)

(52) U.S. Cl.
  CPC ...... *A61M 5/31501* (2013.01); *A61M 5/3129* (2013.01); *A61M 5/31513* (2013.01); *A61M 5/31576* (2013.01); *A61M 2205/273* (2013.01)

(58) Field of Classification Search
  CPC ............ A61M 5/31501; A61M 5/3129; A61M 5/31513; A61M 5/31576
  See application file for complete search history.

(56) References Cited

U.S. PATENT DOCUMENTS

| 4,610,672 A | 9/1986 | Ewalt |
| 4,874,385 A | 10/1989 | Moran |

(Continued)

FOREIGN PATENT DOCUMENTS

| CN | 201768238 U | 3/2011 |
| CN | 104147668 A | 11/2014 |

(Continued)

OTHER PUBLICATIONS

Polypropylene Syringe Filters, 0.22 um, 20mm, Threaded Double Luer Lock, Tisch Scientific, [Post Date unknown], [Site seen Dec. 6, 2021], Seen at URL: https://scientificfilters.com/polypropylene-syringe-filters-spec18197 (Year: 2021).

(Continued)

*Primary Examiner* — Dung T Ulsh
(74) *Attorney, Agent, or Firm* — Renner, Otto, Boisselle & Sklar, LLP

(57) ABSTRACT

In a locking device for locking a plunger rod a plunger rod locking portion is provided for locking a plunger rod of a syringe after use and preventing re-use of the syringe. A chamber is formed inside the plunger rod locking portion for receiving the disc-shaped proximal end of the plunger rod after use of the syringe. The plunger rod locking portion comprises at least one positive locking device configured to positively lock the axial position of the plunger rod by positive-fit engagement with the disc-shaped proximal end of the plunger rod and retain the disc-shaped proximal end of the plunger rod inside the chamber. The locking device provides the functionality of a tamper-evident plunger rod locking device once a dose of medication has been injected by pushing the plunger rod forward, for preventing inadvertent re-use of the syringe.

18 Claims, 23 Drawing Sheets

(56) References Cited

U.S. PATENT DOCUMENTS

| | | | |
|---|---|---|---|
| 4,946,441 A * | 8/1990 | Laderoute | A61J 1/1406 |
| | | | 604/218 |
| 5,062,833 A | 11/1991 | Perler | |
| 5,358,497 A | 10/1994 | Dorsey | |
| 5,370,620 A | 12/1994 | Shonfeld | |
| 5,417,661 A | 5/1995 | Stringer | |
| 5,667,495 A * | 9/1997 | Bitdinger | A61M 5/315 |
| | | | 604/220 |
| 5,700,247 A | 12/1997 | Grimard et al. | |
| D410,724 S | 6/1999 | Robles et al. | |
| 6,086,568 A | 7/2000 | Caizza | |
| 6,117,112 A | 9/2000 | Mahurkar | |
| 6,368,305 B1 | 4/2002 | Dutton | |
| 6,679,863 B2 * | 1/2004 | Bush, Jr. | A61M 5/508 |
| | | | 604/181 |
| 6,712,787 B1 | 3/2004 | Dysarz | |
| 6,905,478 B2 | 6/2005 | Ingram | |
| D512,627 S | 12/2005 | Okada | |
| D581,527 S | 11/2008 | Jansen | |
| 7,476,218 B2 | 1/2009 | Bloom | |
| 7,481,797 B2 | 1/2009 | Mahurkar | |
| 8,016,795 B2 * | 9/2011 | Barrelle | A61M 5/284 |
| | | | 604/187 |
| 8,066,668 B2 | 11/2011 | Wayman | |
| 8,075,535 B2 | 12/2011 | Carrel | |
| 8,790,302 B2 | 7/2014 | Wayman | |
| D712,503 S | 9/2014 | Aiston | |
| D753,488 S | 4/2016 | Escobar et al. | |
| D765,838 S | 9/2016 | McGarry et al. | |
| 9,561,327 B2 | 2/2017 | Mottola | |
| 9,597,455 B2 | 3/2017 | Schiff | |
| D790,691 S | 6/2017 | Davis et al. | |
| D794,187 S | 8/2017 | Dolk et al. | |
| D812,223 S | 3/2018 | Evans et al. | |
| 10,010,682 B2 | 7/2018 | Adam | |
| D866,323 S | 11/2019 | Miksovsky et al. | |
| D869,933 S | 12/2019 | Lee | |
| 10,537,683 B2 | 1/2020 | Ruddocks et al. | |
| D905,041 S | 12/2020 | Ahn | |
| D911,813 S | 3/2021 | Pyle et al. | |
| D922,572 S | 6/2021 | Bertrand et al. | |
| 2001/0053886 A1 * | 12/2001 | Caizza | A61M 5/3234 |
| | | | 604/110 |
| 2005/0070854 A1 * | 3/2005 | Wright | A61M 5/3234 |
| | | | 604/110 |
| 2010/0063451 A1 | 3/2010 | Gray et al. | |
| 2012/0150129 A1 | 6/2012 | Jin et al. | |
| 2015/0045740 A1 | 2/2015 | Kojima | |
| 2016/0361523 A1 | 12/2016 | Haughton | |
| 2017/0143892 A1 | 5/2017 | Schiff | |
| 2017/0239425 A1 * | 8/2017 | Castanon | A61M 5/3293 |
| 2019/0388660 A1 | 12/2019 | Negre | |
| 2020/0405963 A1 | 12/2020 | Combes et al. | |
| 2021/0077738 A1 | 3/2021 | Dadachanji | |

FOREIGN PATENT DOCUMENTS

| | | |
|---|---|---|
| CN | 105031772 A | 11/2015 |
| CN | 204864383 U | 12/2015 |
| DE | 3811973 A | 8/1989 |
| EP | 337074 A | 10/1989 |
| EP | 1092445 A | 4/2001 |
| EP | 1377331 A | 1/2004 |
| EP | 1626760 A | 2/2006 |
| EP | 2445554 A | 5/2012 |
| EP | 2968791 A | 1/2016 |
| EP | 008015283-0004 | 11/2020 |
| JP | 1655598 | 3/2020 |
| KR | 300789526.0000 | 3/2015 |
| KR | 301053854.0000 | 4/2020 |
| KR | 301075728.0000 | 9/2020 |

OTHER PUBLICATIONS

Gerresheimer product catalogue; "Gx® syringe systems and glass cartridges.".
HJ19045824 Web page.
Decision to Grant for corresponding Japanese Application No. 2020-012414 dated Oct. 20, 2020 and its English Translation.
Second Office Action for corresponding European Application No. 19 198 135.6 dated Jun. 18, 2021.

* cited by examiner

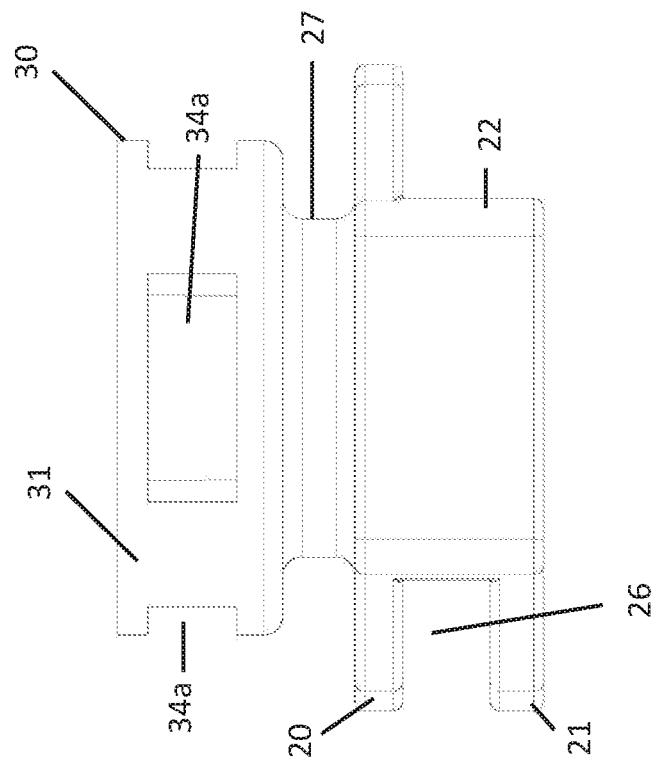
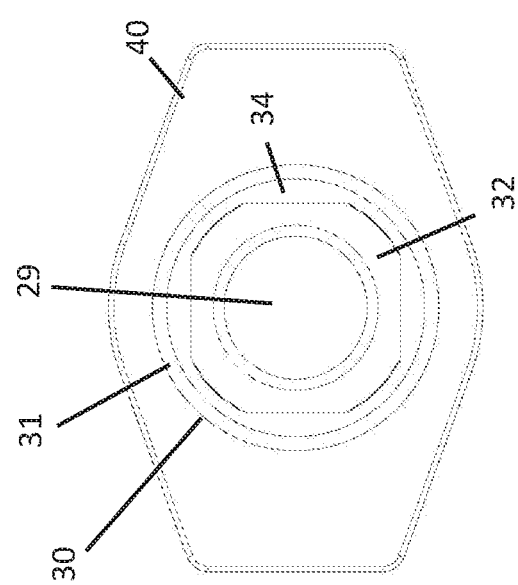
Fig. 7b
Fig. 7c

DEVICE FOR LOCKING A PLUNGER ROD OF A SYRINGE AFTER USE AND PREVENTING RE-USE OF THE SYRINGE, AND SYRINGE ASSEMBLY

FIELD OF INVENTION

The present invention generally relates to drug delivery devices and containers, and more specifically relates to a plunger rod locking device for locking the position of the plunger rod of a syringe at or near a foremost axial position of a distal end of the plunger rod in a syringe barrel after use of the syringe, for preventing re-use of the syringe. A further aspect of the present invention relates to a syringe assembly including such a locking device.

BACKGROUND OF INVENTION

Conventional syringes, which are typically made of plastic or preferably of glass, comprise a barrel having an open proximal end and an opposite distal end. A cylindrical wall extends between these two ends, which defines a substance retaining chamber. An elongate syringe tip projects from the distal end of the syringe barrel and includes a narrow passage which communicates with the substance retaining chamber of the barrel. A plunger may be inserted into the open proximal end of the syringe barrel for sliding in fluid-tight engagement with the cylindrical chamber wall, for sealing the syringe barrel. Sliding movement of the plunger in a distal direction urges fluid in the chamber through the passage in the tip of the syringe for administering the fluid. Conversely, sliding movement of the plunger in a proximal direction draws fluid through the passage in the tip and into the chamber of the syringe barrel.

As the person skilled in the art will appreciate, syringes are intended for a single use only, in part, to address concerns related to the spread of diseases associated with inadvertent re-use of syringes and to deter misuse.

For this purpose, U.S. Pat. No. 5,358,497 discloses a medical locking device that includes a aperture which is positioned at a central position and receives the shaft of the plunger. A retaining member is positioned around the aperture and receives the finger grips of the syringe by engaging at least three sides of the finger grips, to eliminate shifting of the medical locking device. There are opposed cutting members which are chordally positioned in the aperture. The cutting members taper as fine cutting edges for wedging into the plunger during execution of a locking position. If the user twists the plunger into a locking position, the cutting members wedge into the plunger. This locking position eliminates and prevents any further plunger movement in either direction along the longitudinal axis. The device may thus be used as a sort of tamper-evident means for preventing re-use of the syringe.

U.S. Pat. No. 8,066,668 B2 discloses a passive reuse prevention syringe that uses a flange lock, including a locking device. A plunger assembly is disposed at least partially within the syringe barrel, including an elongate plunger rod having a locking flange formed thereon. A plunger head having a distal sealing surface is in engagement with the plunger rod such that the plunger head can move within the chamber of the syringe barrel through an injection cycle. A flange lock is disposed at the open proximal end of the barrel. The flange lock is integral with the open proximal end of the syringe barrel. During the injection cycle, the flange lock engages the locking flange of the plunger rod so as to prevent removal of the plunger rod from the syringe barrel.

US 2005/070854 A1 discloses a syringe. For preventing re-use of the syringe after administering a drug, a plastic collar is clipped onto the enlarged rim at the trailing end of the syringe by means of an annular claw. The trailing end of the collar comprises an annular wall defining a cylindrical recess which is sized to receive the mushroom-shaped grip of the plunger at or near a foremost axial position of the plunger. The inner circumference of the annular wall is very slightly larger than the circumference of the mushroom-shaped grip and thus is sized to receive the grip with a snug fit, so that no surface is available on which a user may get a purchase on the grip. Thus, the user is prevented from retracting the plunger, once the grip has passed the end of the wall. Re-use of the syringe is thus prevented by the geometrical configuration of the collar, but not by a friction lock.

US 2017/239425 A1 discloses a retractable needle syringe. In the embodiment shown in FIGS. 13 and 14, a plunger locking feature is provided by positive-fit engagement members positioned at the proximal end of each of syringe barrel and plunger that once brought in engagement prevent withdrawal of the plunger from the syringe barrel. The positive-fit engagement members are formed integral with the proximal end of each of syringe barrel and plunger, respectively.

U.S. Pat. No. 6,679,863 B2 discloses the positive-fit locking of the grip at the proximal end of the plunger at or near its foremost axial position in a manner similar as disclosed by US 2017/239425 A1.

SUMMARY OF INVENTION

It is an object of the present invention to provide a simple and low-cost integrated plunger rod locking device for locking the position of the plunger rod of a syringe at or near a foremost axial position of a distal end of the plunger rod in a syringe barrel after use of the syringe and preventing re-use of the syringe. It is a further object of the present invention to provide a syringe assembly consisting of a syringe barrel, a plunger and a plunger rod configured for locking the position of the plunger rod of the syringe at or near a foremost axial position of a distal end of the plunger rod in the syringe barrel after use of the syringe and preventing re-use of the syringe According to the present invention there is provided a locking device for locking a plunger rod of a syringe after use, wherein the syringe includes a barrel having an open proximal end and a flange provided adjacent said open proximal end, wherein the barrel is configured to receive the plunger rod through said open proximal end, and a proximal end of the plunger rod is formed disc-shaped. The locking device comprises a mounting portion configured for mounting the locking device to the flange adjacent said proximal end by positive-fit, and a plunger rod locking portion for locking an axial position of the plunger rod after use of the syringe, wherein a communication channel is formed in the locking device for enabling insertion of the plunger rod into the open proximal end of the barrel via the plunger rod locking portion and the mounting portion.

According to the present invention a width of the communication channel is larger inside the plunger rod locking portion to form a chamber or receiving space for receiving the disc-shaped proximal end of the plunger rod after use of the syringe, wherein the plunger rod locking portion comprises at least one positive locking device configured to positively lock the axial position of the plunger rod by positive-fit engagement with the disc-shaped proximal end of the plunger rod, for locking the plunger rod at or near a foremost axial position of a distal end of the plunger rod in the barrel after use of the syringe.

Thus, the locking device according to the present invention provides the functionality of a tamper-evident plunger rod locking device for reliably locking the plunger rod at the proximal end of the barrel once a dose of medication has been injected by pushing the plunger rod forward, for preventing inadvertent re-use of the syringe. The plunger rod locking portion reliably prevents withdrawal of the plunger rod from the syringe barrel back beyond the region of the at least one locking device provided in the plunger rod locking portion, as the disc-shaped proximal end of the plunger rod remains received in the chamber or receiving space and is shielded by side-walls or shielding webs of the plunger rod locking portion against access to the disc-shaped proximal end of the plunger rod from outside the chamber or receiving space.

For ejecting a medical dose, a user will intuitively operate the disc-shaped portion to push the plunger rod toward the distal end of the syringe barrel. As the disc-shaped portion is provided at the very proximal end of the plunger rod, the locking device according to the present invention enables a very intuitive and unambiguous indication of use of the syringe: a) if the disc-shaped proximal end of the plunger rod is fully accommodated in the plunger rod locking portion and thus does not protrude beyond a proximal end of the plunger rod locking portion this will be a clear and unambiguous indication for the user that the syringe has been used already; b) on the other hand, if the plunger rod is in a fully retracted position, which might depend on the dose actually filled in the syringe barrel, this will be a clear and unambiguous indication for the user that the syringe has not yet been used; c) any intermediate position of the disc-shaped portion of the plunger rod between the fully inserted (locked) position and the fully retracted position will be a clear and unambiguous indication for the user that the syringe has been used already, thus causing the user to be very cautious when using the syringe.

Particularly the locking of the disc-shaped proximal end of the plunger rod inside the chamber or receiving space of the plunger rod locking portion enables a clear, unambiguous and intuitive distinction between any unused or partially used condition of the syringe and a condition after use of the syringe with complete or nearly complete ejection of the medical dose initially filled in the syringe barrel. After use of the syringe, the disc-shaped proximal end of the plunger rod is basically trapped in the chamber or receiving space of the plunger rod locking portion and cannot be operated anymore.

The foremost axial position of the plunger rod in the syringe barrel may be identical with the axial position of the plunger in the syringe barrel, if the plunger rod is positively locked without clearance in axial direction. According to a further embodiment the plunger rod may also be positively locked with a certain clearance in axial direction, in which case the plunger rod, together with the plunger, may be pushed further towards the distal end of the syringe barrel, to thus enable that a residual dose of liquid may be injected by further pushing forward the plunger rod toward the distal end of the syringe barrel after the proximal end of the plunger rod has slid beyond the region of the at least one positive locking device. According to the present invention the function of reliably preventing re-use of the syringe may be implemented at low costs and with reduced space requirement by means of a single device. The locking device according to the present invention can be used easily and intuitively. The locking function may be inspected visually, particularly the tamper-evident locked position of the plunger rod may be recognized easily, even by untrained personnel. Even if the locked position of the plunger rod should not be recognized by staff, re-use of the syringe is reliably prevented.

According to a further embodiment the plunger rod locking portion is integrally formed with the mounting portion. Thus, the locking device according to the present invention may be provided even as an integral member, e.g. by plastic injection molding technology.

According to a further embodiment the plunger rod locking portion comprises a circumferential side-wall and the at least one positive locking device is each provided on an inner side of the circumferential side-wall. The circumferential side-wall further secures the tamper-proof condition of the plunger rod, once the plunger rod has been trapped by being positively locked by the at least one positive locking device, because access to the at least one positive locking device from outside the plunger rod locking portion for manipulating the position of the at least one positive locking device can be reliably excluded. After use, the disc-shaped portion at the proximal end of the plunger rod will not protrude beyond the proximal upper rim of the circumferential side-wall of the plunger rod locking portion.

According to a further embodiment a stop surface is provided at a bottom of said chamber for defining the foremost axial position of the distal end of the plunger rod in the barrel by abutment of the disc-shaped proximal end of the plunger rod with the stop surface. The stop surface reliably prevents the disc-shaped proximal end of the plunger rod from being pushed further forward beyond this stop surface. At the same time, the stop surface, which may be formed as a ring, may further enhance the mechanical strength and stability of the chamber or receiving space of the plunger rod locking portion.

According to a further embodiment the at least one positive locking device is configured to retain the disc-shaped proximal end of the plunger rod inside the chamber and to prevent withdrawal of the disc-shaped proximal end of the plunger rod toward a proximal end of the plunger rod locking portion beyond a minimum distance to a proximal upper rim of the plunger rod locking portion, when the axial position of the plunger rod is positively locked, wherein the minimum distance corresponds at least to an axial length of the at least one positive locking device. This minimum distance of the disc-shaped proximal end to the proximal upper rim of the plunger rod locking portion further assists in preventing access to the disc-shaped proximal end for unauthorized manipulation thereof once the disc-shaped proximal end has been caught inside the chamber or receiving space of the plunger rod locking portion by positive-fit locking.

According to a further embodiment the chamber formed by the plunger rod locking portion is configured for preventing full access to the disc-shaped proximal end of the plunger rod from outside the plunger rod locking portion, to prevent withdrawal of the disc-shaped proximal end of the plunger rod out of chamber or receiving space, when the axial position of the plunger rod is positively locked. For this purpose, the plunger rod locking portion may be formed by a circumferential side-wall, wherein the at least one positive locking device is each provided on an inner side of the circumferential side-wall, or the plunger rod locking portion may be formed as a cage-like cylindrical member formed by two annular webs interconnected by axial connecting webs, wherein the at least one positive locking device is each provided on an inner side of an annular web or of an axial connecting web.

According to a further embodiment the at least one positive locking device is each formed as a locking nose radially protruding into the plunger rod locking portion and being configured for positive-fit engagement with the disc-shaped proximal end of the plunger rod. Here, the disc-shaped proximal end of the plunger rod represents the portion of the plunger rod having the maximum outer dimension, which can be easily trapped by the at least one locking nose extending into the inner volume of the plunger rod locking portion.

Of course, according to other embodiments positive locking of the plunger rod may also be accomplished by means of other positive locking devices, such as a rack provided near the proximal end of the plunger rod.

According to a further embodiment the at least one locking nose is each formed in a window or cutout formed in the circumferential side-wall, each of the at least one locking nose having a beveled upper surface facing towards a proximal open end of the plunger rod locking device and a bottom side extending radially inwards and perpendicular to the circumferential side-wall. The locking nose may each be formed as a resilient plate-shaped member pivotally supported at one end thereof on the inner surface of the circumferential side-wall, so that the proximal end of the plunger rod may be trapped inside the plunger rod locking portion at low force, by simply sliding the proximal end of the plunger rod (which is preferably disc-shaped) beyond the at least one locking nose while flexing or bending the locking nose outward toward the circumferential side-wall.

According to a further embodiment a width of the communication channel is larger inside the plunger rod locking portion to form a chamber for receiving the disc-shaped proximal end of the plunger rod, and wherein a stop surface is provided at a bottom of said chamber for limiting or defining the foremost axial position of the plunger rod in the syringe barrel. Thus, the disc-shaped member at the proximal end of the plunger rod may be a little wider than the shaft portion of the plunger rod, which assists to ensure an easy trapping of the proximal end of the plunger rod by positive fit with the at least one locking nose. At the same time, the bottom of the chamber of the plunger rod locking portion serves as a stop for precisely defining the foremost position of the proximal end of the plunger rod inside the chamber of the plunger rod locking portion and thus the foremost position of the plunger inside the syringe barrel.

According to a further embodiment a height of the chamber in an axial direction of the locking device is larger than a thickness of the disc-shaped proximal end of the plunger rod. Thus, a residual dose of liquid may be injected by further pushing forward the plunger rod toward the distal end of the syringe barrel after the disc-shaped proximal end has slid beyond the locking noses, until the disc-shaped proximal end finally abuts against the stop surface at the bottom of the plunger rod locking portion, defining the foremost axial position of the plunger inside the syringe barrel.

According to a further embodiment the mounting portion comprises an upper plate directed towards the proximal end of the communication channel and a bottom plate opposite to said upper plate, an interspace being formed between the upper and bottom plate. Thus, the shape of the two plates may be mated easily to the shape of the finger rest or flange provided at the proximal end of the syringe barrel, thus enabling an intuitive and simple mounting of the locking device. Particularly, the shape of the two plates may be such as to ensure a positive engagement of the mounting portion with the finger rest or flange provided at the proximal end of the syringe barrel, particularly by clipping the mounting portion onto the finger rest or flange.

Here, at least one protrusion is provided for reducing the width of the communication channel to a dimension which is less than a maximum outer dimension (particularly outer diameter) of the plunger inserted into the syringe barrel. Thus, the locking device according to the present invention also provides the additional functionality of a backstop device for preventing inadvertent removal of a plunger from a syringe, because in a condition where the position of the plunger rod is not yet locked by the plunger rod locking portion, a rearward movement of the plunger rod will be automatically stopped once the plunger contacts the at least one protrusion in the communication channel, thus preventing a further displacement of the plunger toward the proximal end of the syringe barrel beyond the predetermined end position defined by the at least one protrusion in the communication channel.

This at least one protrusion may be formed as a semi-circular edge at a proximal end of the mounting portion protruding from the upper plate into the interspace. The shape of the protruding semi-circular edge may assist to ensure a reliable positive fit of the mounting portion on the finger rest or flange provided at the proximal end of the syringe barrel, as the protruding semi-circular edge may be a little resilient and thus flex a little when pushing the mounting portion onto the finger rest or flange of the syringe barrel. At the same time the shape of the semi-circular edge may be precisely mated to the shape of the outer surface of the syringe barrel at the proximal end thereof, thus serving as a kind of stop when pushing the mounting portion onto the finger rest or flange of the syringe barrel to define a locked home position of the locking device on the finger rest or flange of the syringe barrel.

According to a further embodiment this semi-circular edge may have a tapered profile having an outer diameter corresponding to the inner diameter of the barrel at the open proximal end.

If required, the tapered profile may further assist the sliding of the shaft of the plunger rod over the semi-circular edge when inserting the plunger rod into the syringe barrel. Particularly, the plunger rod may be guided with reduced clearance inside the communication channel when inserted into the syringe barrel for coupling with the plunger already provided inside the syringe barrel.

According to a further embodiment the semi-circular edge has a tapered profile having an outer diameter corresponding to the inner diameter of the syringe barrel at the open proximal end. The at least one protrusion, particularly the semi-circular edge, may thus be inserted slightly into the open proximal end of the syringe barrel, which assists in establishing a reliable positive-locking of the mounting portion on the flange at the open proximal end of the syringe barrel. More specifically, when the at least one protrusion, particularly the semi-circular edge, is inserted into the open proximal end of the syringe barrel, the locking device is prevented from inadvertently slipping from the flange of the syringe barrel.

According to a further embodiment the height of the interspace formed between the upper and bottom plate of the mounting portion basically corresponds to the height of the flange at the open proximal end of the barrel. The flange at the open proximal end of the syringe barrel may thus be clamped or at least snuggly fit between the upper and bottom plate of the mounting portion, which further assists in establishing a positive-locking of the mounting portion at the flange. As the at least one protrusion preferably protrudes from the upper plate of the mounting portion, the at least one protrusion thus needs to be inserted into the open proximal end of the syringe barrel for mounting, which further assists in establishing a positive-locking of the mounting portion at the flange, as outlined above.

According to a further embodiment at least a bottom end of the at least one protrusion is resilient or flexible, which can be implemented easily by forming the whole locking device of a resilient plastic material, particularly using injection molding technology. When mounting the locking device on the flange at the open proximal end of the syringe barrel, the at least one protrusion may thus be deformed or flexed slightly, but will then return to a relaxed home position for establishing the positive-locking of the mounting portion at the flange, as outlined above.

According to a further aspect of the present invention there is provided a syringe assembly for medical purposes, comprising: a syringe barrel having a distal end, an open proximal end opposite to the distal end, a sidewall extending between the distal end and the open proximal end defining a chamber, and a flange provided adjacent said open proximal end; a plunger disposed within the chamber of the syringe barrel; and a plunger rod associated with the plunger and connected with the plunger. According to the present invention the syringe assembly further comprises a locking device as set forth hereinafter in more detail, for preventing inadvertent removal of the plunger from the syringe barrel, said locking device being mounted to the flange adjacent said proximal end by positive-fit.

As will become apparent to the person skilled in the art when studying the disclosure of the present invention, the plunger rod locking function may also be implemented in combination with the backstop function for preventing inadvertent removal of the plunger from the syringe barrel. Thus, a further aspect of the present invention that relies on the same inventive concept of the locking device as outlined above and that may be claimed by means of a separate independent set of claims is directed to a locking device for preventing inadvertent removal of a plunger from a syringe, said syringe including a barrel having an open proximal end and a flange provided adjacent said open proximal end, said barrel being configured to receive a plunger rod through said open proximal end, comprising a mounting portion configured for mounting the locking device on the flange, wherein a communication channel is formed in the locking device for enabling insertion of the plunger rod into the open proximal end of the barrel, and at least one protrusion is provided for reducing a width of the communication channel at least in sections, for preventing inadvertent removal of the plunger from the syringe.

According to this second independent aspect of the present invention a plunger rod locking portion as outlined above is additionally provided for locking an axial position of the plunger rod, wherein the communication channel extends through the plunger rod locking portion and the plunger rod locking portion comprises at least one positive locking device configured to positively lock the axial position of the plunger rod by engagement with a proximal end of the plunger rod or with a portion of the plunger rod near the proximal end thereof, for locking the plunger rod at or near a foremost axial position of a distal end of the plunger rod in the barrel.

OVERVIEW ON DRAWINGS

The invention will now be described by way of example and with reference to the accompanying drawings, from which further features, advantages and problems to be solved will become apparent. In the drawings:

FIG. 6a is a sectional view of the proximal end of the syringe barrel with the plunger locking device in the nearly locked condition of the plunger rod according to FIG. 5a;

FIGS. 7b to 7d show the plunger rod locking device of FIG. 7a in a top view and in two side views;

FIGS. 7f and 7g is a sectional view of the proximal end of the syringe barrel with the plunger locking device in the nearly locked condition and in the locked condition of the plunger rod according to FIG. 7a;

FIG. 7h is a sectional view of a syringe barrel when the disc-shaped proximal end of the plunger rod is nearly locked in the plunger rod locking portion of the plunger locking device according to FIG. 7a;

FIG. 7i is a sectional view of a syringe barrel when the disc-shaped proximal end of the plunger rod is locked in the plunger rod locking portion of the plunger locking device according to FIG. 7a;

In the drawings, the same reference numerals designate identical or substantially equivalent elements or groups of elements.

DETAILED DESCRIPTION OF PREFERRED EMBODIMENTS

Figure 1A:
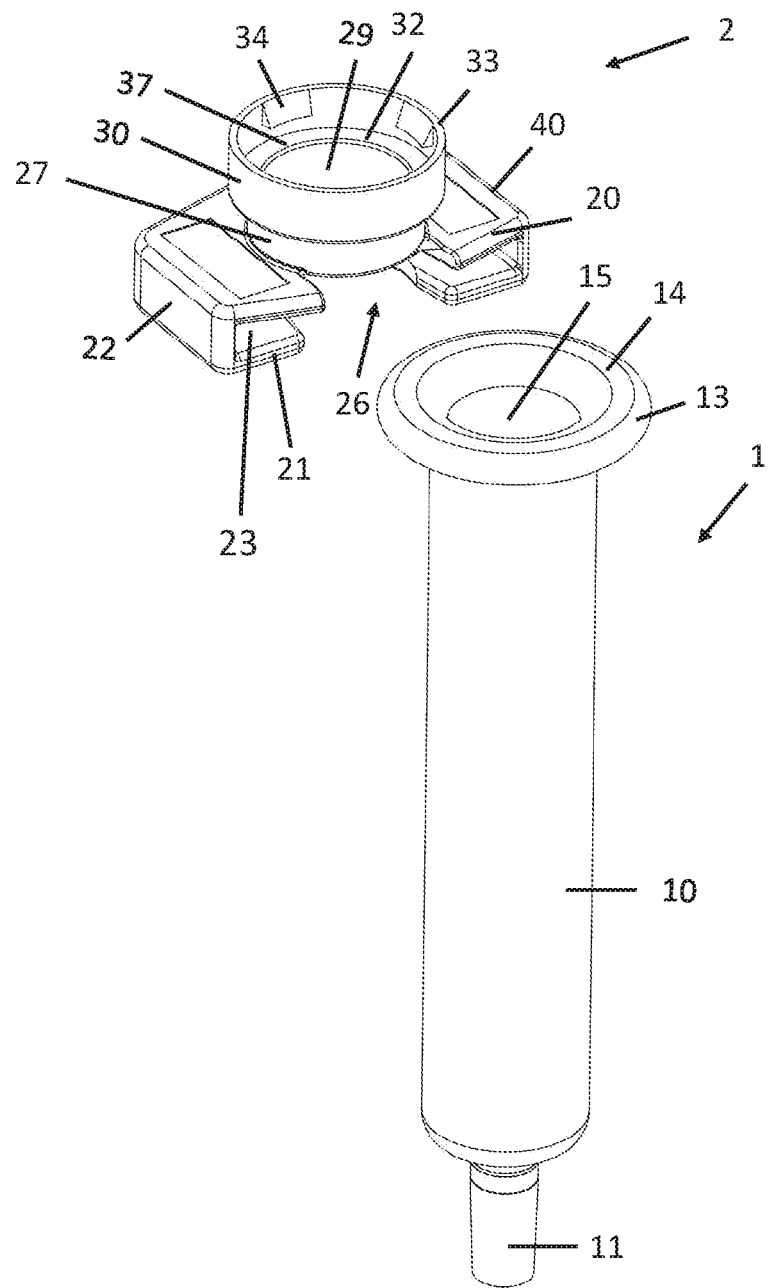
FIGS. 1a and 1b show a syringe barrel with a plunger rod locking device according to the present invention in an unmounted condition and in a mounted condition.
Figure 1B:
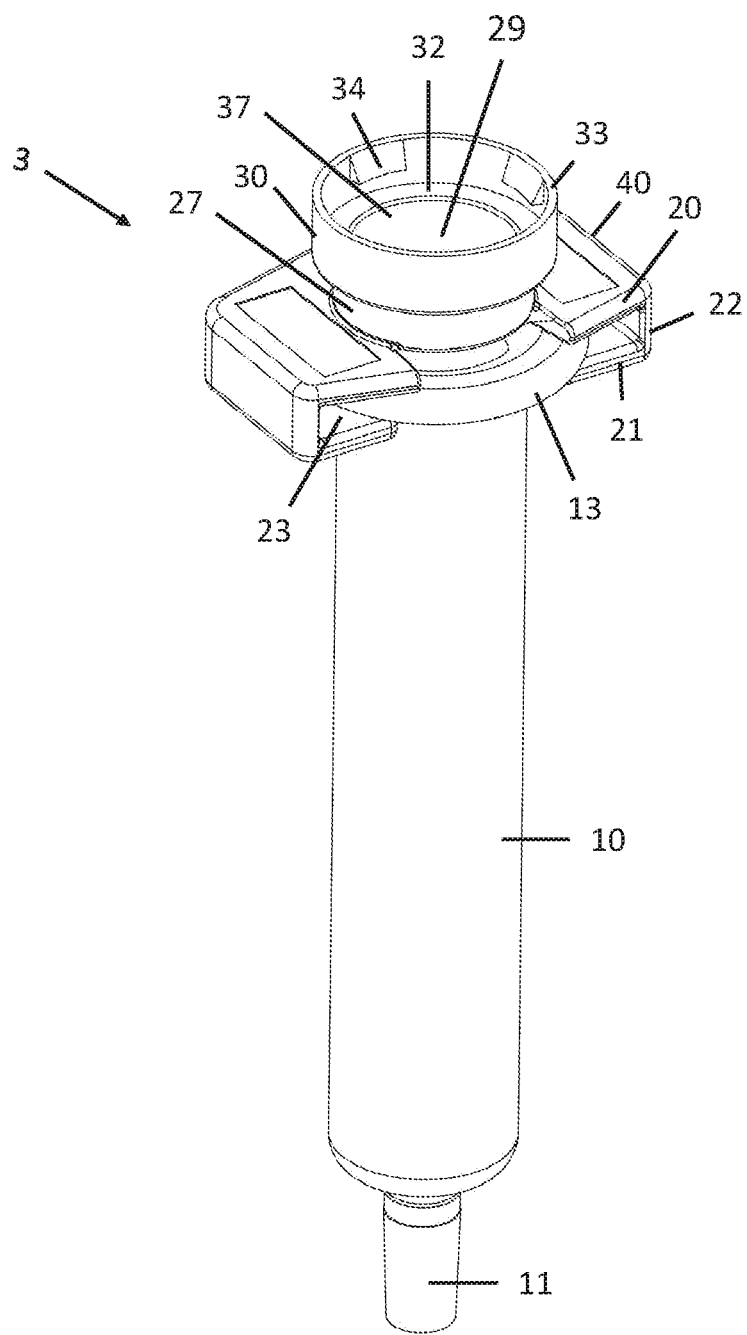

As shown in FIG. 1a, a syringe 1 for use together with the locking device according to the present invention includes a syringe barrel 10 which is formed from glass or plastic material and is preferably transparent. The syringe barrel 10 includes an open proximal end 15 having a flange 13, a distal end 11 and is a cylindrical body formed by a cylindrical side-wall defining a substance receiving chamber which may be pre-filled with a selected dose of medication in either dry or liquid form, as well as other substances such as water or diluent for use in reconstituting a medicament. The distal end 11 of syringe barrel 10 includes a tip having a passage 12 (cf. FIG. 4b) extending in axial direction therethrough and communicating with the substance receiving chamber 16. A plunger rod (now shown) may extend into the open proximal end 15 of the syringe barrel 10 via the open proximal end 15, which serves as a filling opening, and may include a plunger (not shown), which may slide in fluid-tight engagement inside the cylindrical wall to seal the syringe barrel 10. Usually, the plunger rod will be releasably coupled to the plunger, e.g. by a thread. The syringe barrel 10 may be used with a standard needle assembly (not shown), which is generally known from the prior art.

At the distal end 11, the syringe barrel 10 generally does not have an integral collar for engaging the mounting hub of the needle assembly. For this purpose, a collar, particularly a luer collar, may be mounted to the syringe tip at the distal end 11 of the syringe barrel 10.

The needle assembly may be maintained separate from the syringe barrel 10, and may be mounted to the syringe barrel 10 a short time prior to usage of syringe 1. As an example, a needle may be coupled with the syringe tip 11 by means of a standard Luer-lock. In this way, the syringe barrel 10 may be pre-filled with medication, and stored in its pre-filled condition prior to mounting the needle assembly thereto.

The present invention shall, however, not be construed to be limited to a coupling of the needle assembly with the syringe barrel 10, but the needle may also be fixed to the syringe tip 11 in a conventional manner, such as gluing.

To prevent contamination or leakage of medication stored in syringe barrel 10, a resilient closure (not shown) usually will seal the syringe tip at the distal end 11 before use. The resilient closure is preferably made of an elastomeric material and comprises a cylindrical body (not shown), which is inserted into the distal end 11 to seal it. In order to keep the resilient closure in place, in a proper engagement with the syringe tip at the distal end 11 and to prevent a contamination of the resilient closure during storage, a tip cap assembly such as the one disclosed in US 2013/0338603 A1 may be provided on the syringe tip at the distal end 11 of the syringe barrel 10.

In order to seal the opposite proximal end 15 of the syringe barrel 10, a resilient plug is inserted into the syringe barrel 10 via the open proximal end 15, which will be in fluid-tight engagement with the cylindrical wall of syringe barrel 10, to thereby seal the substance receiving chamber.

At the opposite proximal end 15 of the syringe barrel 10 a flange 13 is provided forming a type of finger rest permitting the user to manipulate the syringe during use. The flange 13 may take various shapes such as rounded as shown in FIG. 1a or, as oftentimes seen, a type of modified rounded, which may include a pair of straight sides, as the person skilled in the art will appreciate. The inner edge 14 of the flange 13 may be rounded, as shown in FIG. 1a.

Overall, the rounded inner edge 14 at the open proximal end may be funnel-shaped towards the inner surface of the cylindrical side-wall 10, as shown in FIG. 1a.

For locking the plunger rod after use of the syringe and preventing re-use of the syringe, a locking device generally designated by reference numeral 2 is mounted on the flange 13 at the open proximal end 15 of syringe barrel 10. The locking device 2 includes a mounting portion 40 configured for mating with syringe barrel 10 via the flange 13, to be positively mounted onto the flange 13. Particularly, the locking device 2 may be clipped against a certain minimum resistance onto the flange 13, but may be removed again from the flange 13 by applying a force which exceeds this resistance.

Turning now more specifically to FIGS. 2a to 2f, in one embodiment of the locking device 2 according to the present invention the mounting portion 40 includes an upper plate 20 and a bottom plate 21, spaced apart from one another so as to create therebetween a pocket-type interspace 23, which is dimensioned and configured to snuggly accommodate therein the flange 13 of the syringe 1. If desired, bottom plate 21 may be eliminated in favor of a top plate extension portion which locks about flange 13.

The interspace 23 may include a frontal opening 26 through which flange 13 enters interspace 23 for mounting the locking device 2 at the flange 13. The frontal opening 26 is configured and dimensioned in a manner to permit the mounting of mounting portion 40 over flange 13 over a wide range of angles of approach or orientation between flange 13 and mounting portion 40. Side walls 22 of the mounting portion 40 may serve to connect top and bottom plates 20 and 21, respectively, and help define interspace 23. These side-walls 22 may be provided only along the two narrow sides of the locking portion 40, as shown in FIG. 1a, or may be provided along the two narrow sides and additionally along a rear long side of the locking portion 40. Generally, the height of interspace 23 corresponds to the axial length of flange 13.

While the top and bottom plates 20 and 21 are herein depicted as relatively flat, if desired, either one or both of them can be formed with a concave shape such that the plates 20, 21 are free to flex towards and away from interspace 23. In this manner, either or both of the top and bottom plates 20, 21 may flex as the mounting portion 40 of locking device 2 is placed about flange 13, thereby accounting for any tolerance deviations, inconsistencies of shape or surface, or other difficulties displayed by the flange 13. Also, in this manner, mounting portion 40 may exert a more positive holding action onto flange 13, should such increased force be necessary or desirable. A certain flexing may also assist in defining a minimum force required for mounting the mounting portion 40 onto the flange 13, particularly by clipping. While not depicted in the drawings, the person skilled in the art will also appreciate that the locking device in general may be dimensioned and configured so that the plates 20, 21 may assume a convex shape to achieve the same purpose.

Bottom plate aperture 26 is generally configured and dimensioned for form fitting contact with the exterior surface of syringe barrel 10 at the open proximal end 15 thereof. The aperture 26 itself and/or the structure associated therewith forms a passageway through upper plate 20 having a width that may be somewhat smaller than the internal diameter defined by open proximal end 15 of syringe barrel 10, but that may also correspond to the internal diameter defined by open proximal end 15 of syringe barrel 10. As herein shown, bottom aperture 26 is formed in a relatively arcuate manner so as to conform to the relatively cylindrical outside surface of syringe barrel 10 at the proximal end 15 thereof. More specifically, as shown in FIG. 2b, the inner edge 25 of bottom aperture 26 at the bottom plate 21 has a semi-circular shape of a diameter that is identical to the outer diameter of syringe barrel 10 at the open proximal end 15 thereof or that may be slightly smaller than this outer diameter.

According to further embodiments, the width of the aperture 26 formed in the upper plate 20 may also be slightly smaller than the outer diameter of syringe barrel 10 at the open proximal end 15 thereof to thereby implement an additional backstop function against inadvertent withdrawal of the syringe plunger after mounting the locking device 2 on the flange of the syringe, as outlined in more detail hereinafter, but which does not represent an essential feature of the plunger rod locking device according to the present invention. However, the shape of the aperture 26 is not necessarily so limited and, as can be appreciated, can be configured to accommodate any shape taken by syringe barrel 10, such as ovoid, square, etc.

Both to permit insertion of locking device 2 about the flange 13 and to permit the insertion of the locking device 2 regardless of the presence or absence of a plunger, the inner edge 25 of bottom plate aperture 26 may be provided with a leading edge 25a formed or otherwise cut through the bottom plate 21. Thus, bottom plate 21 features a lead opening, which is connected to aperture 26 via an opposite pair of transition edges.

Figure 2A:
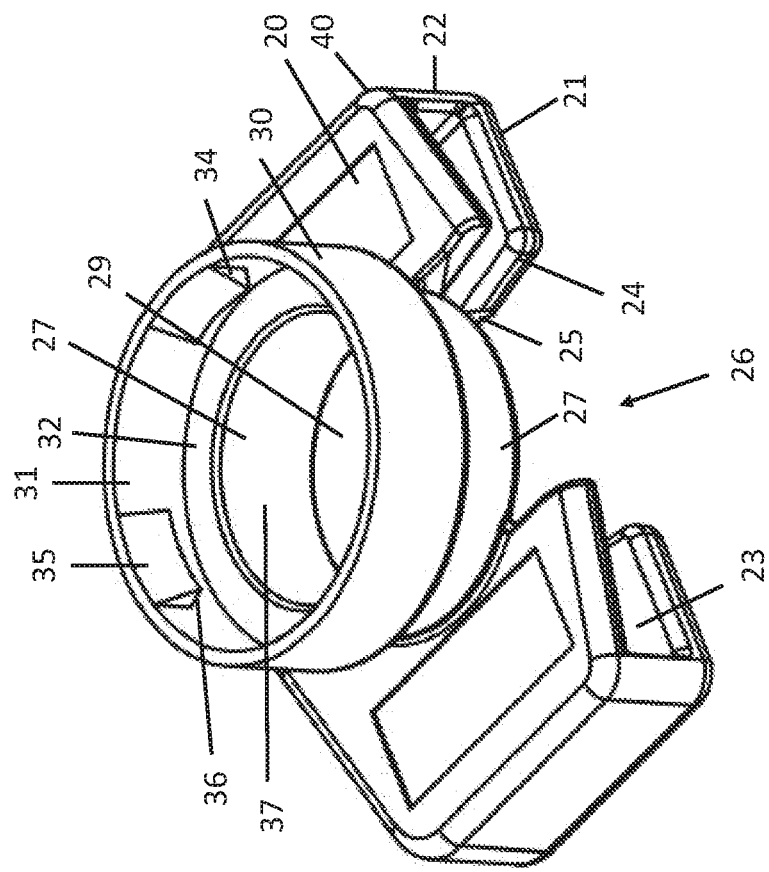
FIG. 2a shows the plunger rod locking device according to a first embodiment of the present invention in a perspective view from a front side.
Figure 2C:
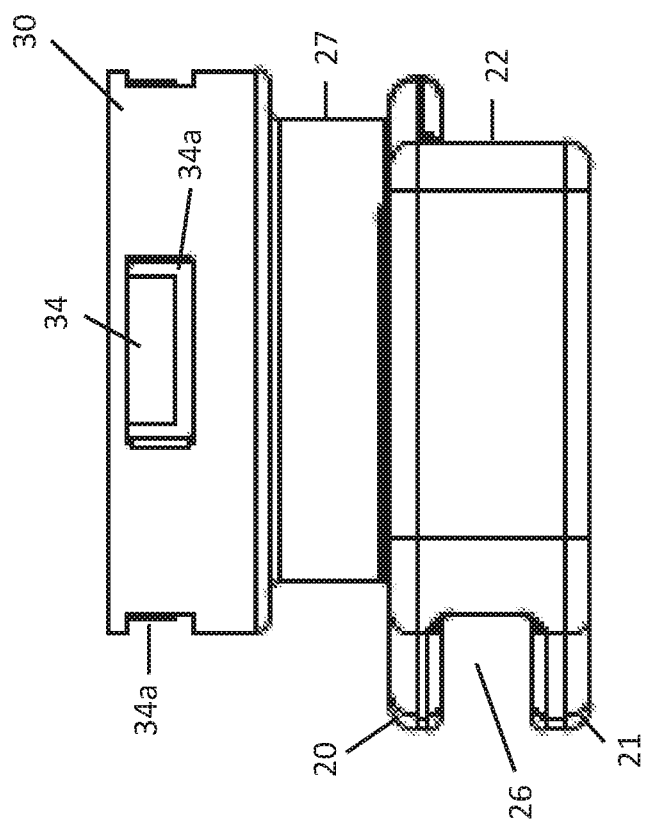
FIGS. 2b to 2d show the plunger rod locking device of FIG. 2a in a top view and in two side views.
Figure 2B:
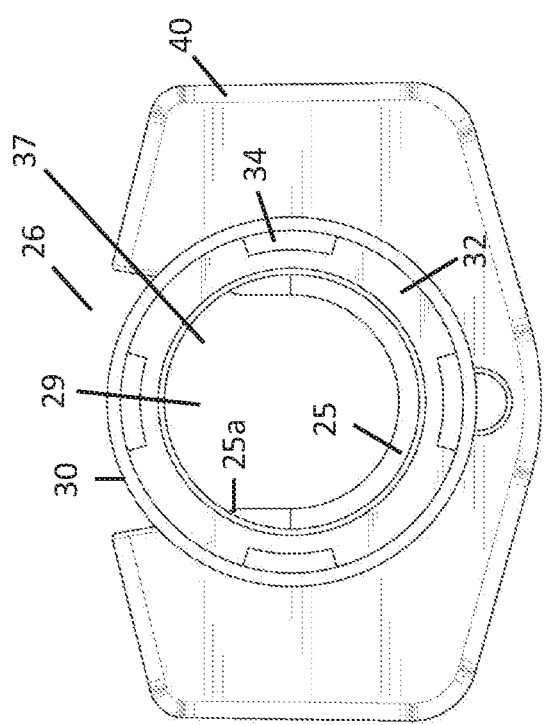
Figure 2E:
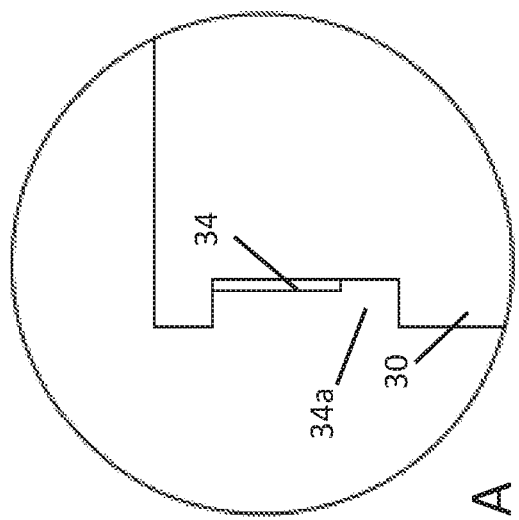
FIG. 2e shows detail A of FIG. 2d.
Figure 2D:
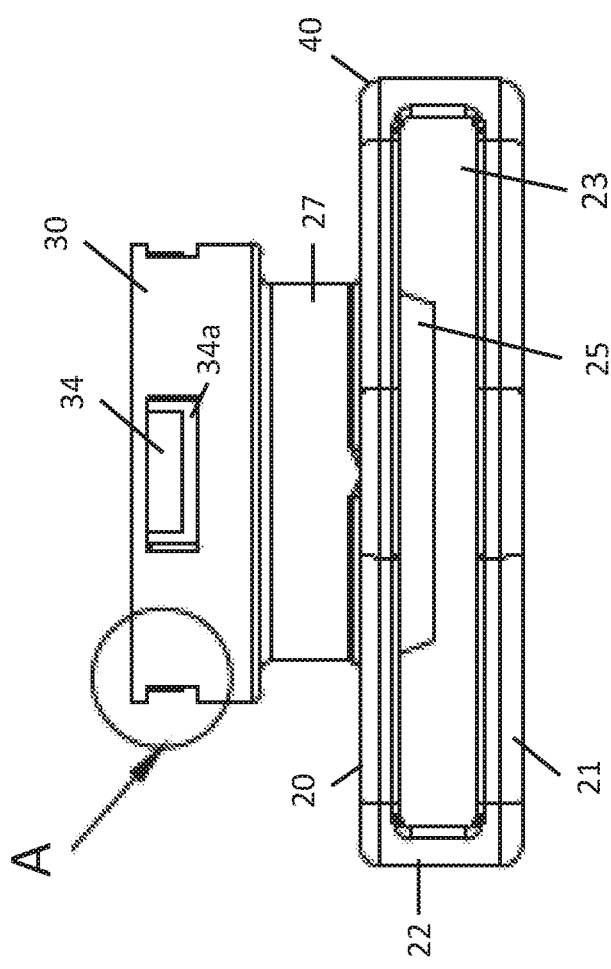
Figure 2F:
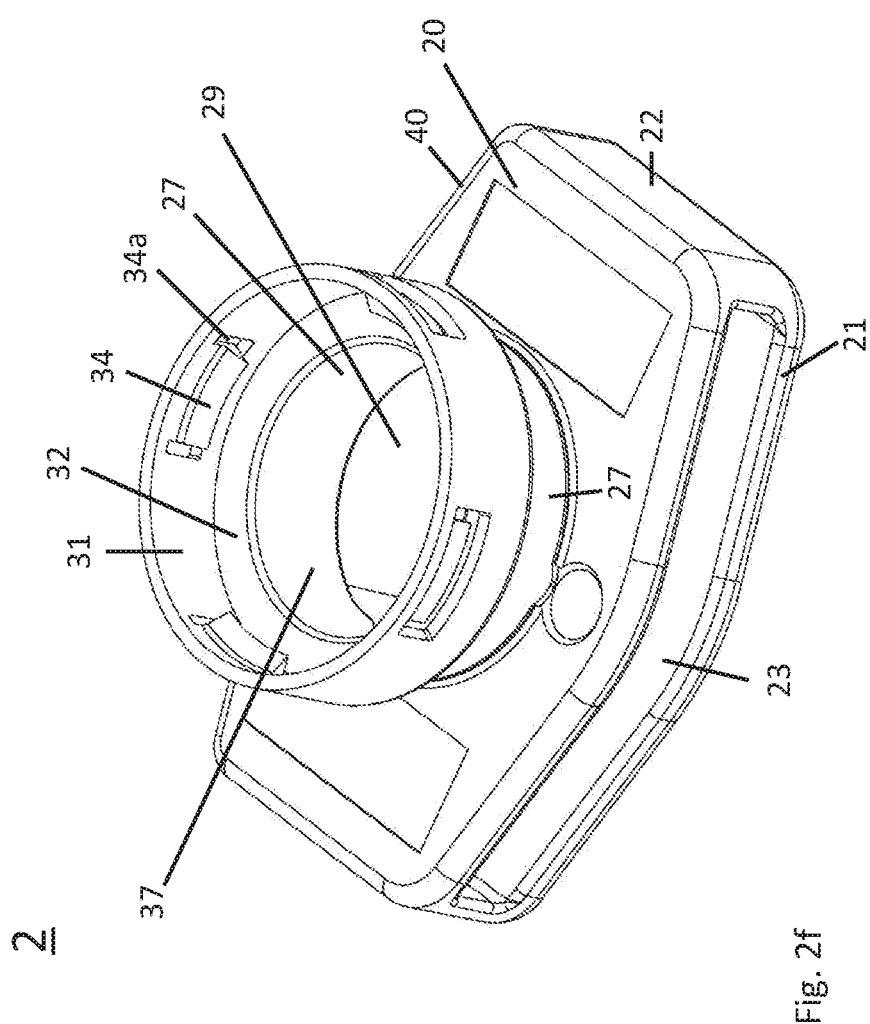
FIG. 2f shows the plunger rod locking device of FIG. 2a in a perspective view from a rear side.

As shown in the sectional view of FIG. 2d, the inner edge 25 may have a truncated (frustro-conical) shape, if viewed in a cross-section view. The inner diameter of the truncated (frustro-conical) inner edge 25 may correspond to the inner diameter of the syringe barrel 10 at the proximal end 15 thereof, or it may be even a little larger. According to this alternative, the truncated (frustro-conical) inner edge 25 would not be suited to implement a backstop function for preventing inadvertent removal of the plunger from the syringe barrel once inserted into the syringe barrel.

According to a further embodiment according to the present invention, however, the outer diameter of the truncated (frustro-conical) inner edge 25 may correspond to the inner diameter of the syringe barrel 10 at the proximal end 15 thereof. More specifically, the proximal end of flange 13 will usually abut (or nearly abut) against the inner surface of upper plate 20 so that the truncated (frustro-conical) inner edge 25 will snuggly fit against the rounded inner edge 14 of flange 13. For this purpose, at least the bottom end of the truncated (frustro-conical) inner edge 25 may also be resilient.

With the semi-circular shape of the inner edge 25, which forms an aperture 26 open towards one longitudinal side of the mounting portion 40, the locking device 2 may be pushed from the side onto the flange 13 of syringe 1. When the mounting portion 40 with the semi-circular aperture 26 is pushed onto the flange 13 of syringe 1, the truncated (frustro-conical) inner edge 25 will be flexed and deformed to slide over the flange 13 of syringe 1, until the truncated (frustro-conical) inner edge 25 will positively fit into the open proximal end 15 of syringe to thereby reliably mount the mounting portion 40 on flange 13 by positive fit. In this position, with the plunger rod (not shown in FIGS. 2a to 2d) extending across the communication channel 29 into the open proximal end 15 of syringe 1, the locking device 2 cannot be removed again from the flange 13. As will become apparent to the person skilled in the art, when pushing the mounting portion 40 onto the flange 13 of syringe, the upper plate 20 and/or bottom plate 21 of the mounting portion 20 may be flexed slightly, to allow the truncated (frustro-conical) inner edge 25 (or the at least one protrusion 28 shown in FIG. 3) to slide into the open proximal end 15 of syringe 1 and abut against the e.g. funnel-shaped rounded inner edge 14 of flange 13.

As shown in FIGS. 2a and 2d, the mounting portion 40 is connected with a plunger rod locking portion 30 disposed above the locking portion 40. More specifically, a relatively short cylindrical connecting portion 27 may be provided between the mounting portion 40 and the plunger rod locking portion 30. Preferably, the plunger rod locking portion 30 is integrally formed with the mounting portion 40, e.g. by plastic injection molding. As an alternative, the plunger rod locking portion 30 and the mounting portion 40 may be formed as separate members connected with each other using fixing members, such as screws or bolts, or using other connecting techniques, such as screwing, adhesive bonding or heat fusion. Here, the plunger rod locking portion 30 is in communication with the mounting portion 40, and a communication channel 29 is formed in the locking device 2 that has a width slightly larger than the outer diameter of the plunger rod so as to enable insertion of a plunger rod from vertically above through the locking device 2 and this communication channel 29 into the inner volume of a syringe barrel.

More specifically, the plunger rod locking portion 30 forms a cylindrical chamber or receiving space 37 formed by the cylindrical side-wall 31, which is configured for receiving the disc-shaped proximal end 50 (see FIG. 4a) of the plunger rod 5, when the plunger rod 5 is locked at or near a foremost axial position of the distal end of the plunger rod 5 in the barrel 10 after use of the syringe.

As shown in FIGS. 2a to 2f, the plunger rod locking portion 30 includes at least one locking device 34 for locking the axial position of the plunger rod, as outlined hereinafter in more detail. In the embodiment of FIGS. 2a and 2d the at least one locking device is embodied as a beveled locking nose 34 which may flex radially outward or may be resilient, for permitting insertion of the proximal end of the plunger rod into the inner volume or chamber 37 formed by the plunger rod locking portion 30 below the beveled locking nose 34.

Preferably, a plurality of locking devices 34, such as the afore-mentioned locking noses, are disposed at equiangular spacing in the plunger rod locking portion 30 to thereby define an inner volume or receiving space for receiving and locking the axial position of the plunger rod at or near a foremost axial position of the plunger rod in the syringe barrel.

As best shown in FIGS. 2a and 2d, the plunger rod locking portion 30 may be formed by a circumferential circular side-wall 31, with the at least one locking nose 34 being integrally formed on an inner surface of circumferential side-wall 31, so that an inner volume or receiving space 37 for locking the axial position of the plunger rod is defined between a bottom side 36 of the at least one locking nose 34 and an annular bottom 32 of the plunger rod locking portion 30. Here, the annular bottom 32 serves as a stop surface for defining the foremost axial position of the plunger rod in the syringe barrel by abutment of the disc-shaped proximal end of the plunger rod with this stop surface 32. This means that the width of the communication channel 29 below the annular bottom 32 is less than the width or diameter of the disc-shaped proximal end 50 of the plunger rod 5 (see FIG. 4a).

According to further embodiments (not shown), however, this stop-function may for defining the foremost axial position of the plunger rod in the syringe barrel also be implemented by means of protrusions protruding into the chamber or receiving space 37 of the plunger rod locking portion 30 at a position below the locking noses 34, in order to stop pushing further forward the disc-shaped proximal end of the plunger rod, to thereby define the foremost axial position of the plunger rod in the syringe barrel by abutment of the disc-shaped proximal end of the plunger rod of such protrusions.

Figure 6A:
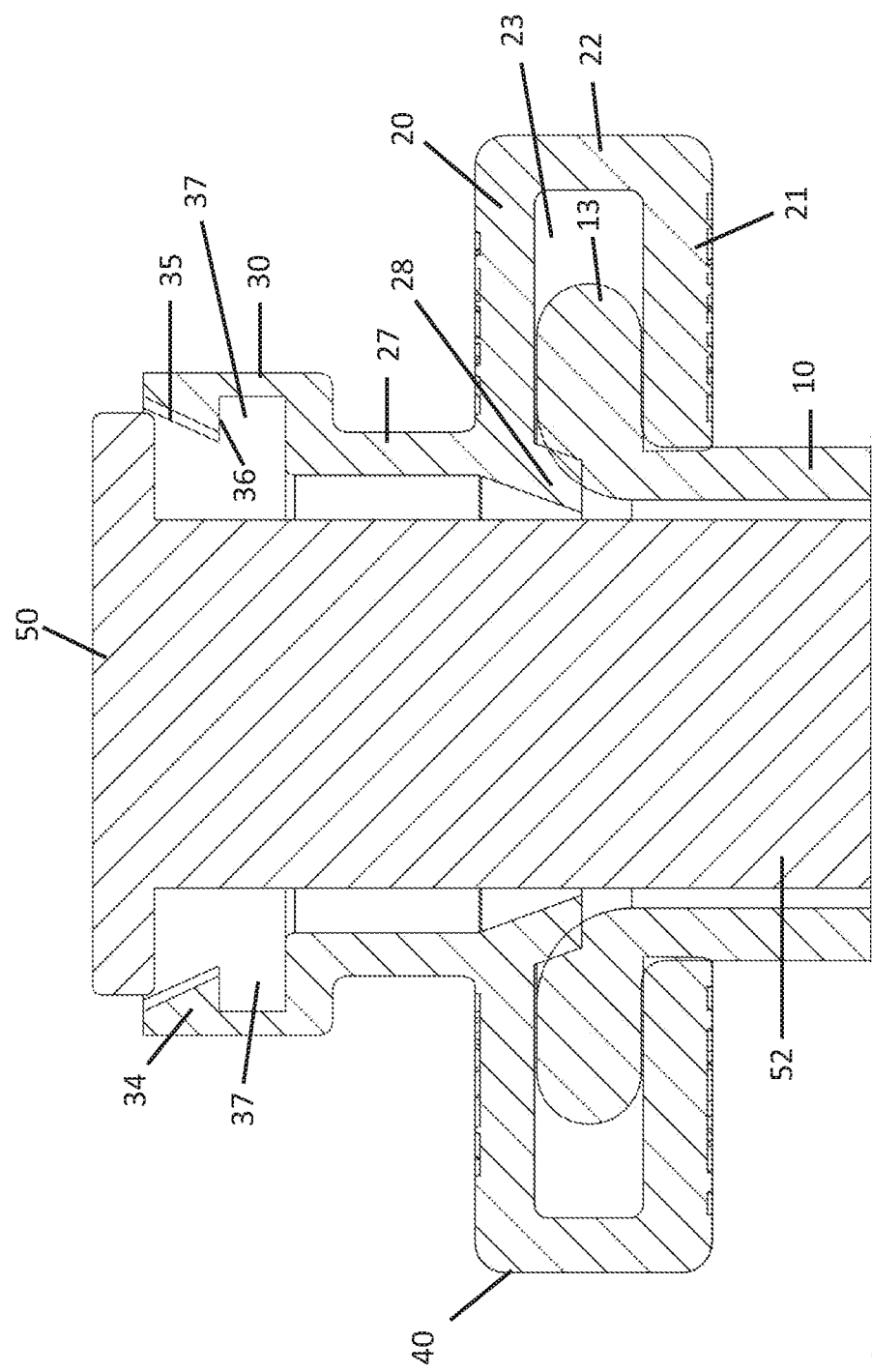
Figure 6B:
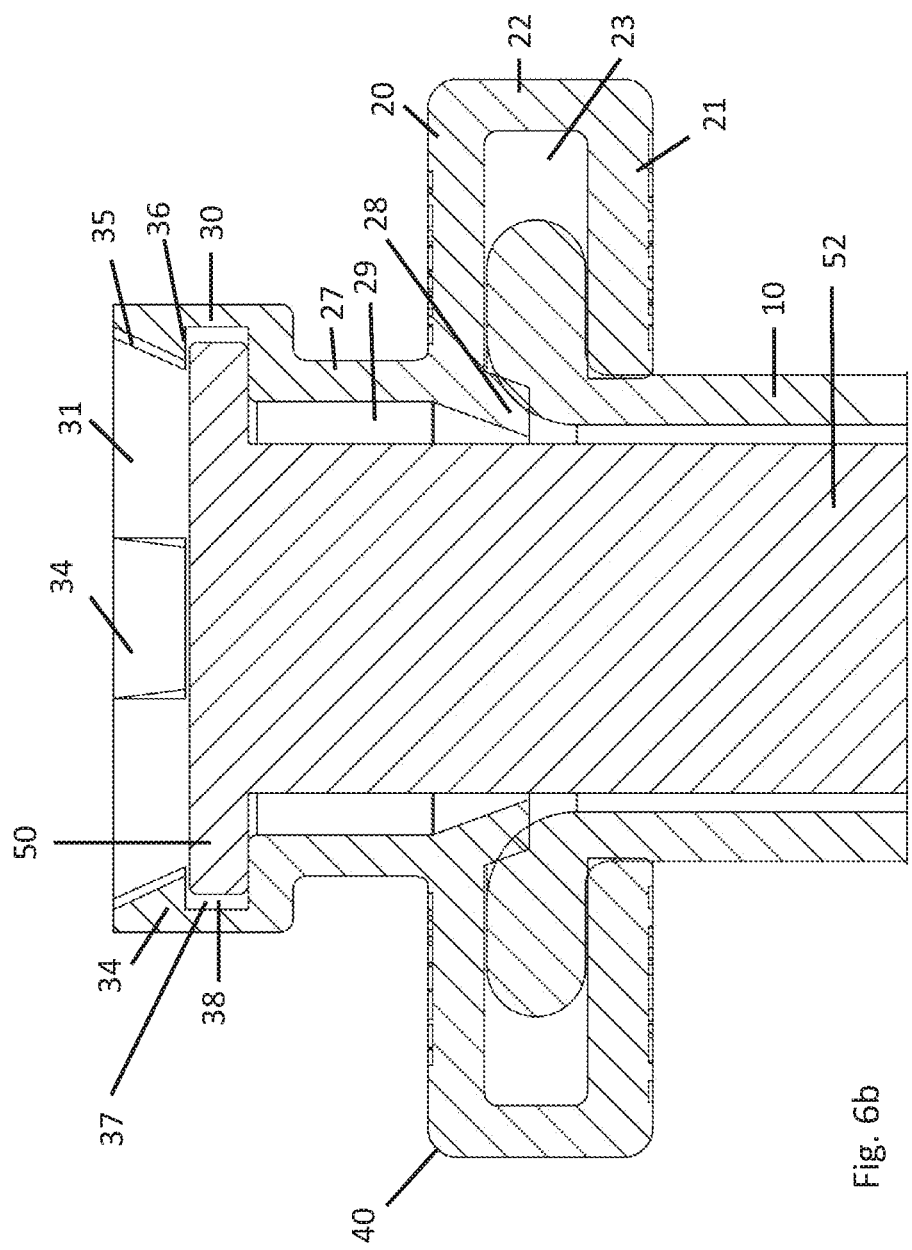
FIG. 6b is a sectional view of the proximal end of the syringe barrel with the plunger locking device in the locked condition of the plunger rod according to FIG. 5b.

When the disc-shaped proximal end of the plunger rod is positively locked by the at least one locking nose 34, as shown in FIG. 6b and explained hereinafter, the disc-shaped proximal end of the plunger rod is completely received in the chamber or receiving space 37 formed by the circumferential side-wall 31 of the plunger rod locking portion 30, more specifically formed between the bottom sides 36 of the locking noses 34 and the stop surface 32. In this locked condition, as shown in FIG. 6b, the circumferential side-wall 31 of plunger rod locking portion 30 thus completely surrounds or covers the proximal end of the plunger rod, for preventing unauthorized access to the disc-shaped proximal end 50 of the plunger rod 5, e.g. for removal from the chamber 37 by releasing the positive-fit of the at least one locking nose 34 by flexing. Thus, the circumferential side-wall 31 further enhances the tamper-proof effect provided by the at least one positive locking device, to thereby prevent inadvertent re-use of the syringe once a medication dose has been injected by pushing the rod up to the foremost axial position in the syringe. In the locked condition, the disc-shaped proximal end 50 of the plunger rod 5 is fully received in the volume or chamber defined by the circumferential side-wall 30, thus providing a clear and unambiguous indication of a used-state of the syringe.

At the same time, the locking noses 34 define a certain minimum distance between the proximal side of the disc-shaped proximal end 50 of the plunger rod 5 and the upper rim of the cylindrical side-wall 31 of the plunger rod locking device 30, to thereby prevent withdrawal of the disc-shaped proximal end 50 of the plunger rod 5 toward a proximal end of the plunger rod locking portion 30 beyond this minimum distance, when the axial position of the plunger rod 5 is positively locked. As can be concluded from FIG. 6b, this minimum distance corresponds at least to the axial length of the locking noses 34, and may be larger than this axial length if the locking noses 34 are disposed a little deeper inside the chamber 37 of the plunger rod locking device 30.

As best shown in FIGS. 2d and 2e, a window or cutout 34a may be formed in the circumferential side-wall 31 of the plunger rod locking portion 30 at each position of the at least one associated positive locking device (e.g. locking nose 34) to further assist a certain flexing of the at least one locking nose 34 toward the circumferential side-wall 31 upon insertion of the plunger rod. As best shown in FIG. 2c, the at least one locking nose 34 may each be formed as a rectangular plate protruding radially inward into the communication channel 29 at an acute angle. The at least one locking nose 34 may be connected to the circumferential side-wall 31 only at an upper (proximal) end thereof, to thereby enable a proper flexing of the at least one locking nose 34 about the upper (proximal) end thereof serving as a fulcrum when the plunger rod is inserted from above into the plunger rod locking portion 30.

Of course, the locking nose 34 may also each be formed as a solid beveled locking nose on the inner surface of the circumferential side-wall 31, without the provision of such windows or cutouts 34a.

Figure 3:
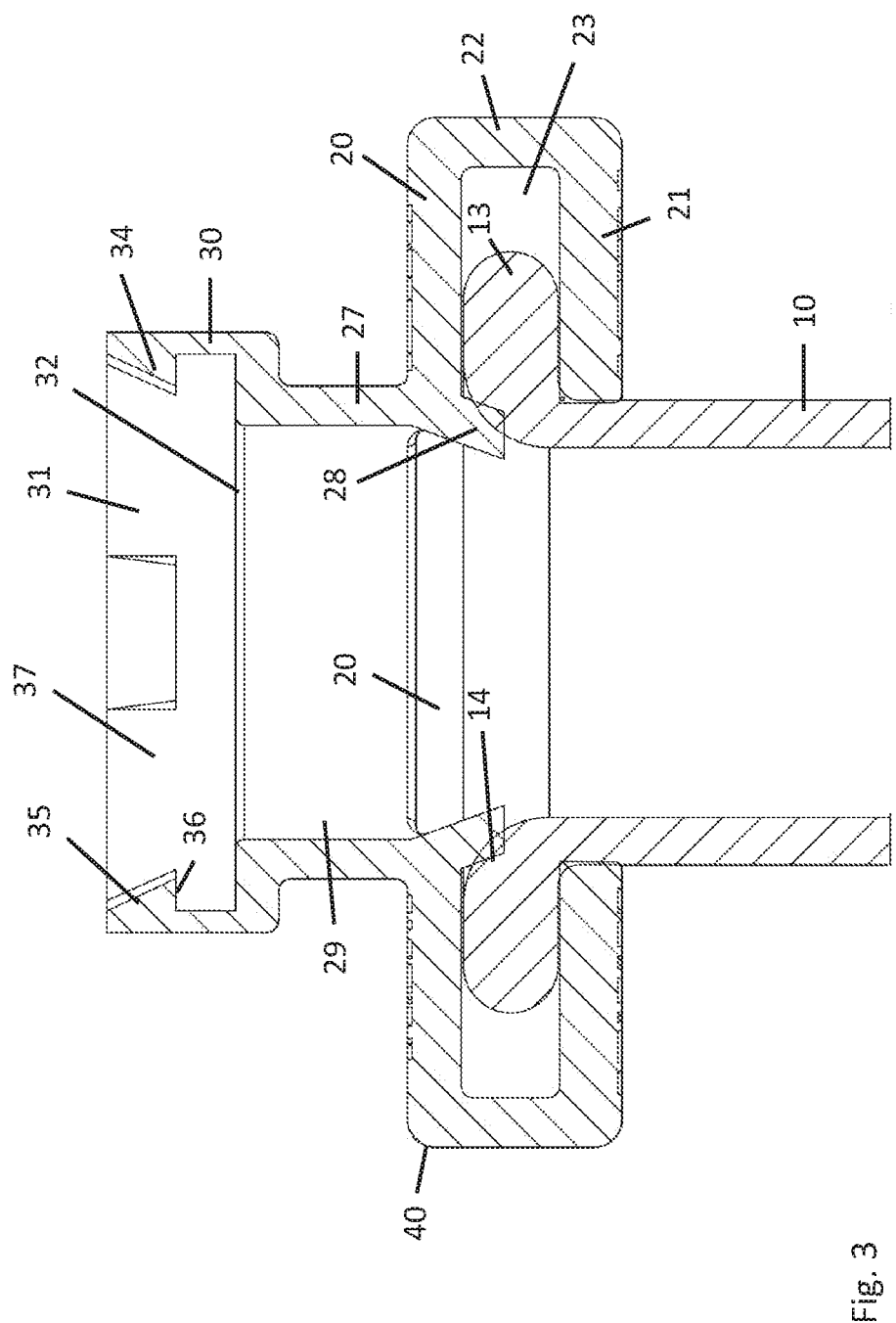
FIG. 3 shows a sectional view of the plunger rod locking device according to a second embodiment of the present invention mounted at the proximal end of a syringe barrel.

FIG. 3 shows a sectional view of the plunger rod locking device according to a preferred further embodiment of the present invention if mounted on flange 13 of syringe barrel 10. According to this embodiment, the plunger rod locking device 2 additionally provides a so-called backstop function for additionally preventing inadvertent removal of the plunger from the syringe barrel. As shown in FIG. 3, at least one protrusion 28 may protrude radially into the tubular communication channel 29 to thereby further reduce the width of the communication channel 29 at least in sections to a width which is slightly smaller than the outer diameter of the plunger (not shown) inserted into the syringe barrel 10, for additionally preventing inadvertent removal of the plunger from the syringe barrel 10. The at least one protrusion 28 may be formed by the inner edge 25 of bottom aperture 26 having a semi-circular shape, but may also be formed as a separate member at the distal surface of the upper plate 20 of the mounting portion 20. E.g. the at least one protrusion 28 may be formed as an axial extension of the connecting portion 27 or of the mounting portion 20. The at least one protrusion 28 positively fits into the open proximal end 15 of syringe barrel 10 to thereby assist in positively fixing the mounting portion 40 at the flange 13. In the mounted condition of the locking device shown in FIG. 3, the interspace 23 of the mounting portion 40 provides for a certain clearance to thereby compensate varying outer diameters of the flange 13.

As best shown in FIGS. 2a and 3, the communication channel 29 extends through the entire locking device 2 in axial direction, including the plunger rod locking portion 30 and the mounting portion 40, and is generally dimensioned to allow unhindered insertion of a syringe plunger therethrough. The communication channel 29 is of a profile corresponding to the base area of the disc-shaped proximal end of the plunger rod, and may be of a generally circular profile in the preferred case that the disc-shaped proximal end of the plunger rod has a circular base area. The communication channel 29 is formed by the inner volume or receiving space 37 of the plunger rod locking portion 30, the inner volume of the connecting portion 27 and by the inner volume of the mounting portion 40. In this embodiment, the minimum diameter of the communication channel 29 corresponds to the outer diameter of the plunger rod, except at the proximal end thereof, which is usually disc-shaped and has a slightly larger outer diameter than the plunger rod. In the mounted condition of the locking device shown in FIG. 3 the communication channel 29 is in communication with the inner volume of syringe barrel 10 to allow insertion of a plunger rod into the syringe barrel via the communication channel 29 and the open proximal end 15. Usually, the plunger will be inserted into the proximal open end 15 of the syringe barrel 10 when the locking device is not yet mounted on the flange 13. However, in an alternative embodiment the plunger may even be inserted into the proximal open end 15 of the syringe barrel 10 when the locking device is already mounted on the flange 13 and when the plunger rod is not yet inserted into the syringe barrel. For this purpose, it is preferred if the at least one protrusion 28 slightly beveled radially inward and downward and only protrudes slightly radially inward into the open proximal end 15, as shown in FIG. 3, so that the plunger will be elastically deformed a little when inserted into the syringe barrel 10 via the communication channel 29 and may expand again with the syringe barrel 10 to slide further toward the distal end of syringe barrel 10 in fluid-tight engagement inside the cylindrical wall of syringe barrel 10.

As will become apparent to the skilled person, the minimum diameter of the communication channel 29 is not necessarily smaller than the maximum outer dimension of the plunger, as the afore-mentioned backstop function for preventing inadvertent removal of the plunger from the syringe barrel represents an optional, additional function of the locking device according to the present invention.

Figure 4A:
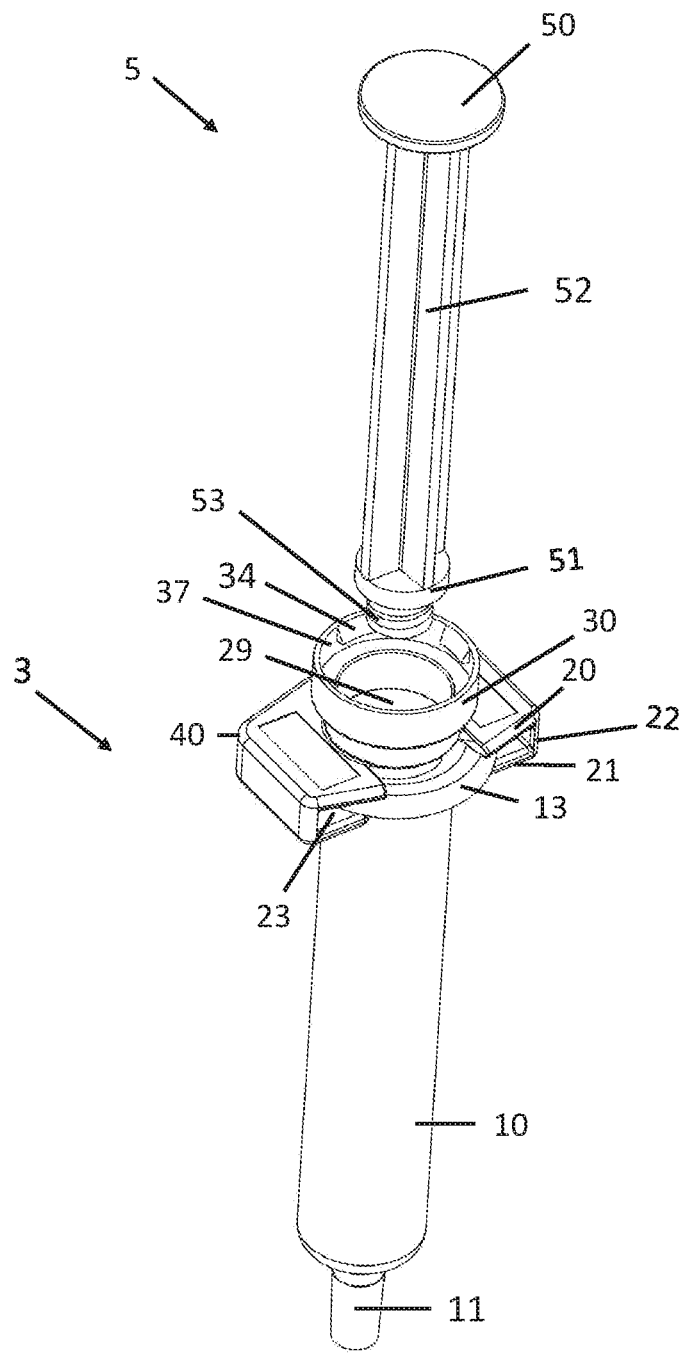
FIGS. 4a and 4b show the insertion of a plunger rod into a syringe barrel with a locking device according to the present invention mounted at the proximal end of the syringe barrel in a perspective view and in a sectional view.

FIG. 4a shows the insertion of a plunger rod 5 from the proximal side via the communication channel 29 into the syringe barrel 10 with the locking device according to the present invention mounted at the proximal end of the syringe barrel 10. At this stage, the plunger has already been inserted into the syringe barrel. The plunger rod 5 includes a shaft 52. As shown in FIG. 4a, the shaft 52 may include a plurality of fins or ribs extending along the length of the plunger shaft 52 and parallel to an imaginary longitudinal axis thereof. As shown in FIG. 4a, the fins or ribs may intersect each other e.g. under a right angle. The proximal end 50 of the plunger rod 5 may be disc-shaped, and is formed in this example by a circular disc 50 having an outer diameter that is larger than the outer diameter of the plunger shaft 52 at all other portions (e.g. in the region of the afore-mentioned fins or ribs). This outer diameter of the disc-shaped proximal end of the plunger rod 5 is smaller than the inner diameter of the plunger rod locking portion 30 (particularly of the circumferential side-wall or receiving volume thereof) but is larger than the clear diameter between the locking noses 34 in the chamber of receiving volume 37 of the plunger rod locking portion 30.

At the opposite distal end 51 of the plunger rod 5 a screw-type or other type of coupling arrangement may be provided for coupling the plunger rod 5 with a plunger (not shown in the drawing). Usually, in the condition of FIG. 4a the plunger will already be inserted into the chamber of the syringe barrel 10 to seal a pre-filled dose of medication inside the chamber.

The plunger rod 5 will thus be inserted via the communication channel 29 of the locking device and the open proximal end of the syringe barrel 10 to get coupled with the plunger by means of the thread 53 or other type of coupling arrangement provided at the distal end 51 of plunger rod 5. For allowing insertion of the plunger rod 5, the inner width at the narrowest portion of the communication channel 29, which is defined e.g. by the protrusion 28 at the distal end of the connecting portion 27 or by the truncated (frustroconical) inner edge 25 (see FIGS. 2b and 2d), should be larger than the maximum outer diameter of the plunger rod, particularly at the distal end 51 thereof.

Figure 4B:
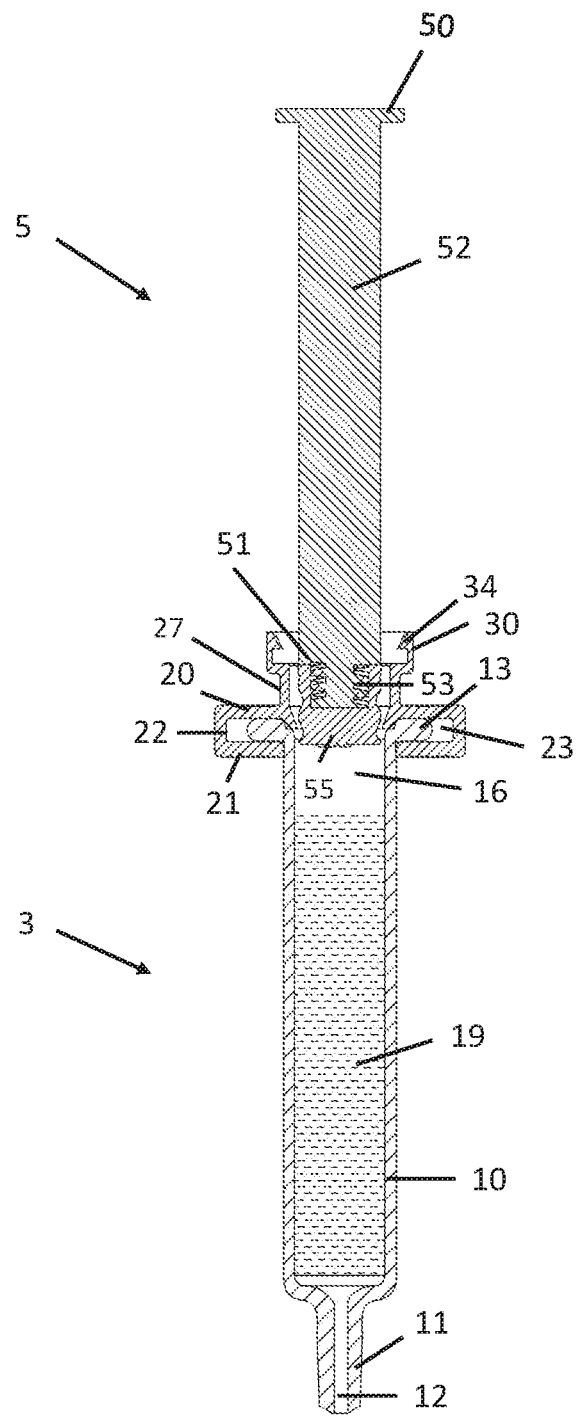

FIG. 4b shows the insertion of the plunger rod 5 into the syringe barrel 10 with the locking device of FIG. 4a in a sectional view when the distal end 51 of the plunger rod 5 is coupled with the plunger 55 inside the chamber 16 of the syringe barrel 10.

Figure 5A:
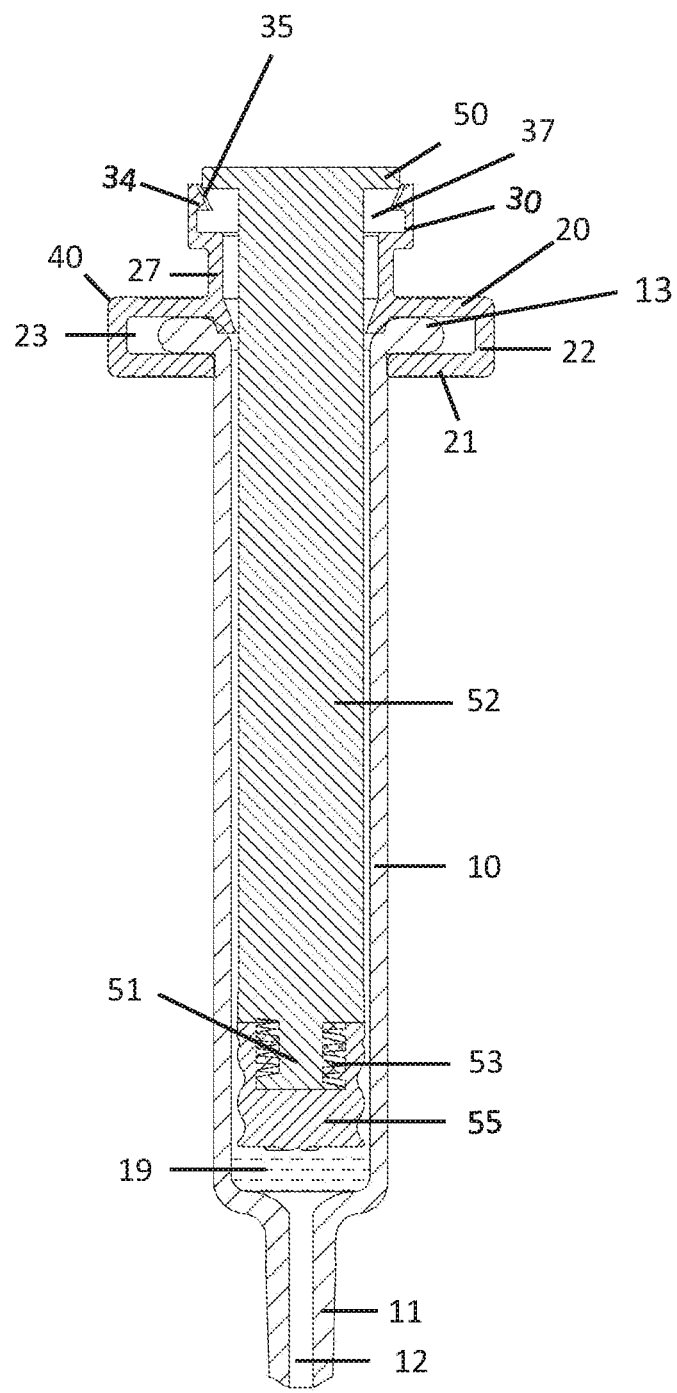
FIG. 5a is a sectional view of a syringe barrel when the disc-shaped proximal end of the plunger rod is nearly locked in the plunger rod locking portion of the plunger locking device according to the present invention.
Figure 5B:
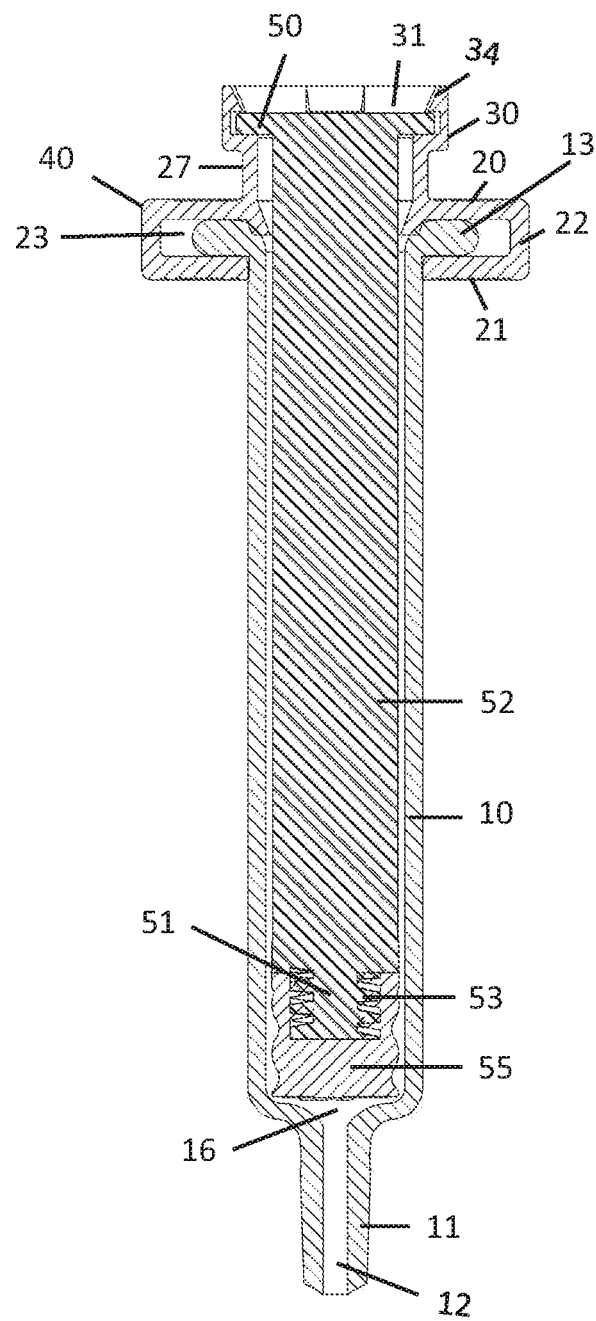
FIG. 5b is a sectional view of a syringe barrel when the disc-shaped proximal end of the plunger rod is locked in the plunger rod locking portion of the plunger locking device according to the present invention.

At this stage, the administering of the liquid 19 via the injection channel and a syringe needle (not shown) may be started by pushing the plunger rod 5 forward, toward the distal end 11 of the syringe barrel 10. Finally, the proximal end 50 of the plunger rod 5 reaches the region of the plunger rod locking portion 30, as shown in FIG. 5a. At this stage the plunger 55 is pushed nearly up to the foremost distal position in the syringe barrel 10 and the disc-shaped proximal end 50 of the plunger rod 5 gets in contact with the bevel 35 of the locking noses 34. When the plunger rod 5 is pushed further forward towards the distal end 11 of the syringe barrel 10, the disc-shaped proximal end 50 starts to slide along the bevels 35 of the locking noses 34, flexing the resilient locking noses 34 increasingly outwards, towards the circumferential side-wall of the plunger rod locking portion 30, and/or causing a certain flexing and bending of the disc-shaped proximal end 50 of the plunger rod 5. As shown in FIG. 5b, finally the disc-shaped proximal end 50 of the plunger rod will have slid beyond the front ends of the bevels 35 of the locking noses 34 to be fully accommodated inside the chamber or receiving volume 37 formed by the circumferential side-wall of the plunger rod locking portion 30. More specifically, the disc-shaped proximal end 50 of the plunger rod will have slid into the interspace formed between the bottom sides 36 of the locking noses 34 (see FIG. 2a) and the annular stop surface 32 at the bottom of the plunger rod locking portion 30, so that the resilient locking noses 34 will flex backward into the communication channel 29 to recapture their home position. In this condition the plunger 55 will have reached its foremost distal position in the syringe barrel 10, as shown in FIG. 5b.

More specifically, according to this embodiment the foremost distal position of the plunger 55 in the syringe barrel 10 is reached when the distal side of the disc-shaped proximal end 50 abuts against the annular stop surface 32 at the bottom of the plunger rod locking portion 30.

As shown in FIGS. 5a and 5b, the height of the chamber or receiving space 37 formed between the bottom sides 36 of the locking noses 34 (see FIG. 2a) and the annular stop surface 32 at the bottom of the plunger rod locking portion 30 in an axial direction of the locking device may be equal to the thickness of the disc-shaped proximal end 50 of the plunger rod 5, so that the disc-shaped proximal end 50 is snuggly received between the bottom sides 36 of the locking noses 34 (see FIG. 2a) and the stop surface 32 at the bottom of the plunger rod locking portion 30 without axial clearance. Anyway, locking of the disc-shaped proximal end 50 of the plunger rod 5 by the locking noses 34 reliably prevents unauthorized release of the plunger rod 5 after injection by withdrawal of the disc-shaped proximal end 50 of the plunger rod 5 from chamber or receiving space 37.

FIG. 6a is a sectional view in the region of the proximal end of the syringe barrel in the nearly locked condition of the plunger rod according to FIG. 5a. FIG. 6b is a sectional view of the proximal end of the syringe barrel in the locked condition of the plunger rod according to FIG. 5b, when the disc-shaped end 50 of the plunger rod is locked basically without play in the interspace between the locking noses 34 and the annular stop surface at the bottom of the chamber or receiving space 37. In this condition the disc-shaped proximal end 50 is fully accommodated and retained in the chamber or receiving space 37 of the plunger rod locking device 30, and an inadvertent removal of the plunger rod is reliably prevented, which serves as a tamper-proof indicator for preventing inadvertent re-use of the syringe once the disc-shaped proximal end 50 of the plunger rod is locked by the locking noses 34.

Figure 7A:
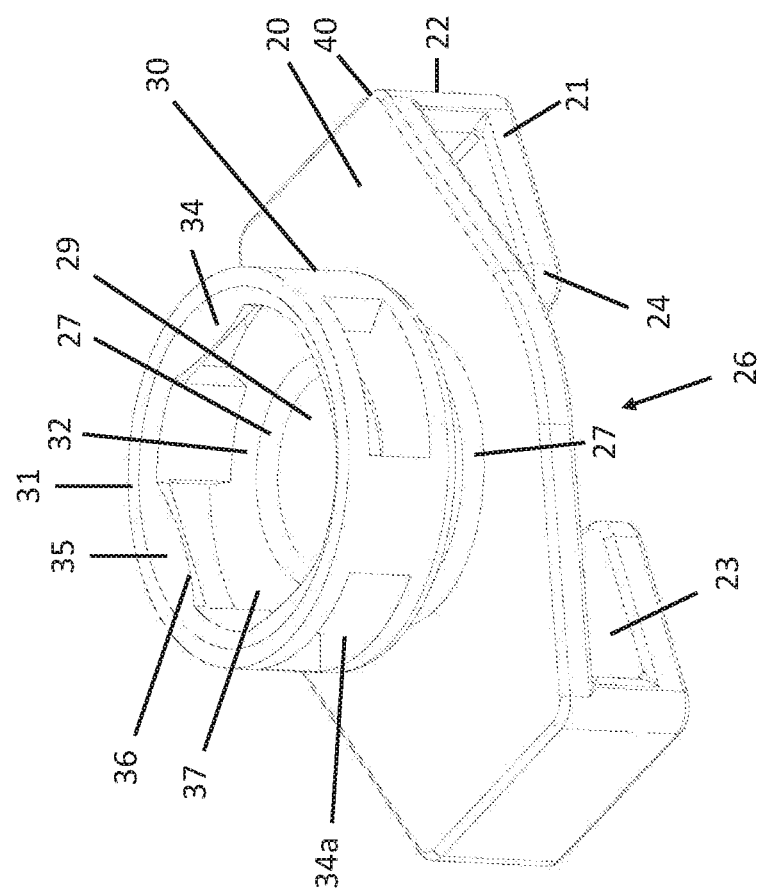
FIG. 7a shows the plunger rod locking device according to a third embodiment of the present invention in a perspective view from a front side.
Figure 7E:
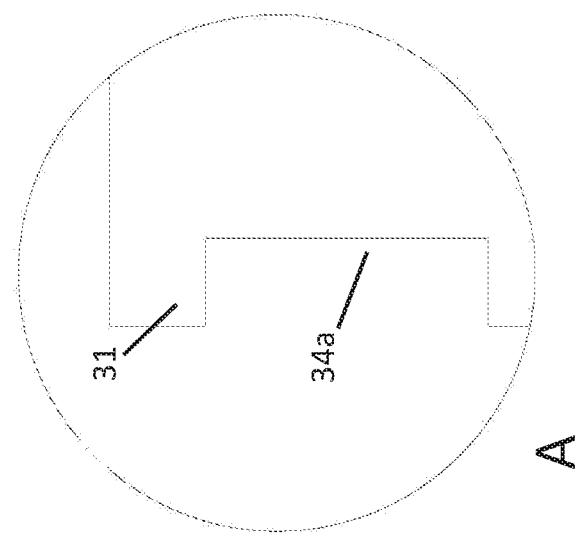
FIG. 7e shows detail A of FIG. 7d.
Figure 7D:
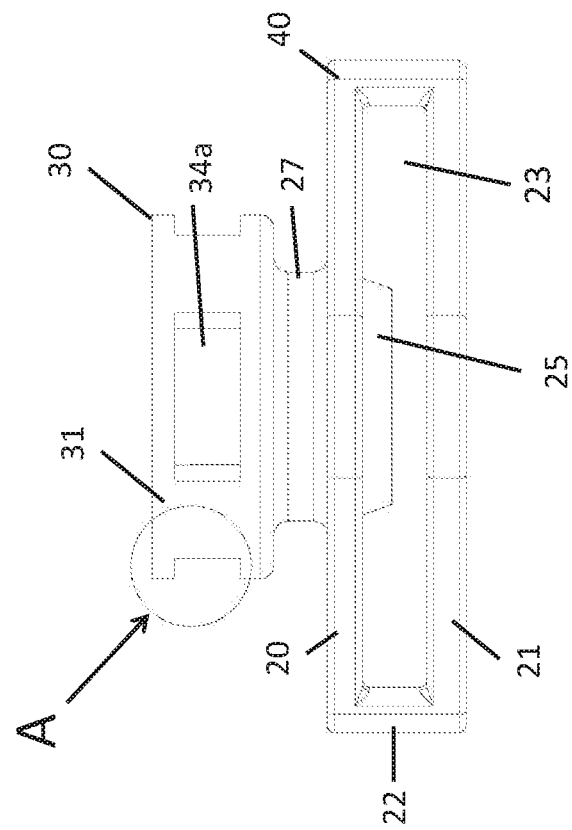

FIGS. 7a to 7e show a further embodiment of the locking device according to the present invention. Here, in comparison to the afore-mentioned first embodiment the chamber or receiving space 37 of the plunger rod locking portion 30 has a more open, filigree structure in that relatively large windows 34a are formed in the otherwise circumferential side-wall 31 forming the chamber or receiving space 37 of the plunger rod locking portion 30. More specifically, a plurality of rectangular windows 34a, e.g. four windows 34a, may be provided at equiangular spacing along the otherwise circumferential side-wall 31, which are interrupted by axial connecting webs connecting the annular upper rim of the circumferential side-wall 31 with the bottom 32 of the plunger rod locking portion 30. As shown in FIG. 7a, locking noses 34 are each formed above a corresponding window 34a. As shown in the plan view of FIG. 7b, these locking noses 34 have linear front edges which form lateral edges of a virtual square of a side length, which is slightly less than the maximum outer width of the disc-shaped proximal end of the plunger rod (not shown) to be locked by these locking noses. Also, in this embodiment, the upper surfaces of the locking noses 34 are formed as bevels 35 that are slanted inward and downward under an acute angle toward the chamber 37 formed by the circumferential side-wall 31. The bottom surfaces 36 of the locking noses 34 may extend perpendicular to the circumferential side-wall 31, to thereby prevent an inadvertent release of the disc-shaped proximal end of the plunger rod once it is locked in the interspace between the locking noses 34 and the annular bottom 32 of the plunger rod locking portion 30.

Figure 7F:
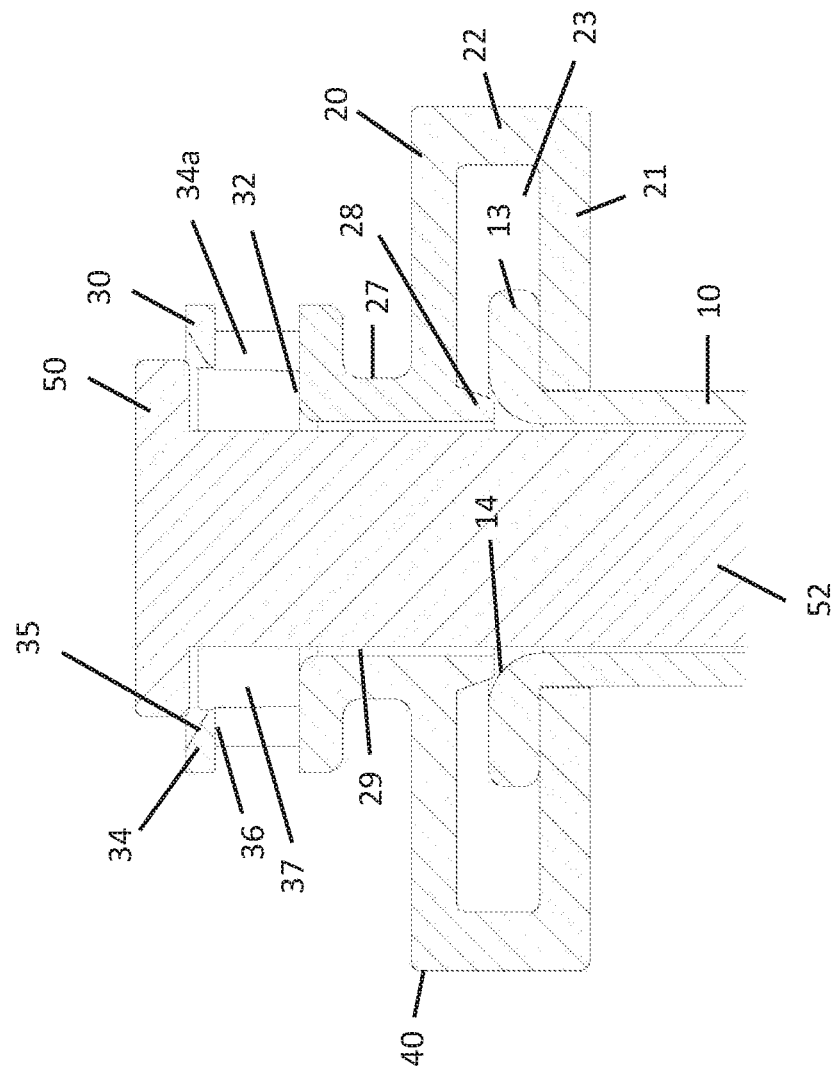
Figure 7G:
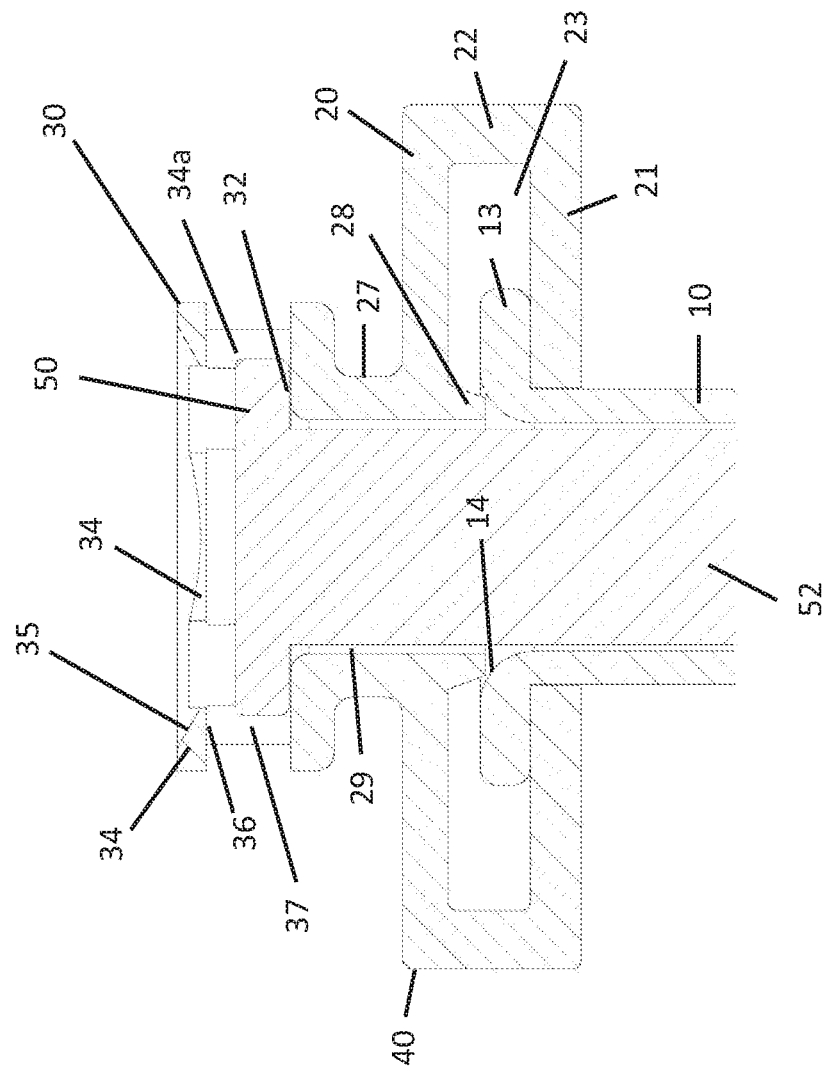
Figure 7H:
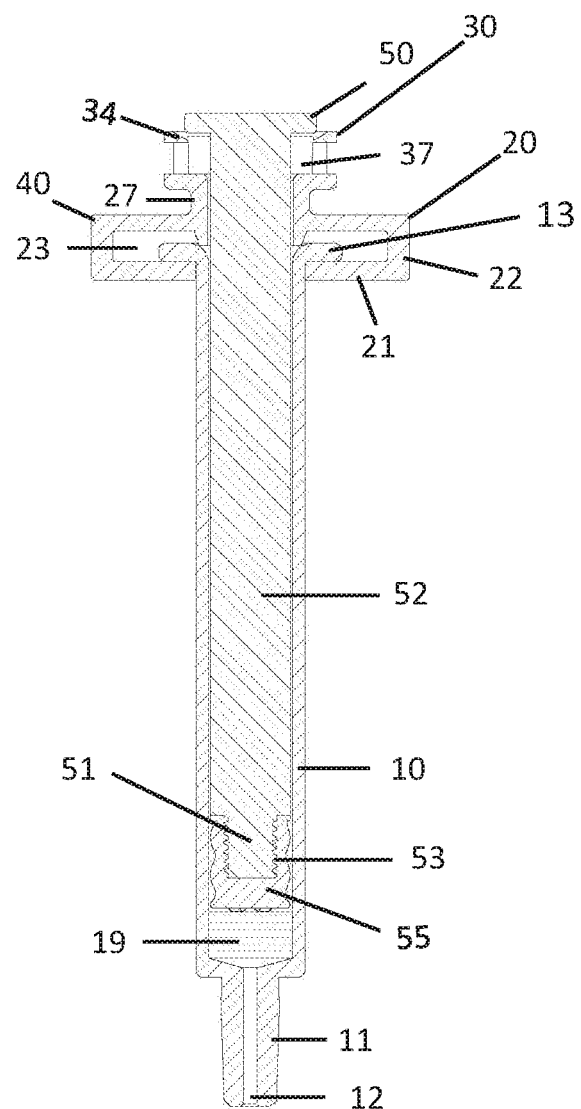

FIG. 7f is a sectional view in the region of the proximal end of the syringe barrel in the nearly locked condition of the plunger rod locking device according to FIG. 7a. FIG. 7g is a sectional view of the proximal end of the syringe barrel in the locked condition of the plunger rod locking device according to FIG. 7a, when the disc-shaped end 50 of the plunger rod is locked with axial play in the interspace between the locking noses 34 and the annular stop surface 32 at the bottom of the chamber or receiving space 37. In the condition of FIG. 7g the disc-shaped proximal end 50 is fully accommodated and retained in the chamber or receiving space 37 of the plunger rod locking portion 30, and an inadvertent removal of the plunger rod by withdrawal of the disc-shaped proximal end 50 of the plunger rod from the chamber or receiving space 37 is reliably prevented, which serves as a tamper-proof indicator for preventing inadvertent re-use of the syringe once the disc-shaped proximal end 50 of the plunger rod is locked by the locking noses 34. At the same time, the disc-shaped end 50 and the plunger rod 50 may be moved in axial direction over a certain minor distance as the axial length of the disc-shaped end 50 is less than the distance between the bottom surfaces 36 of the locking noses 34 and the stop surface 32 at the bottom of chamber 37.

Figure 7I:
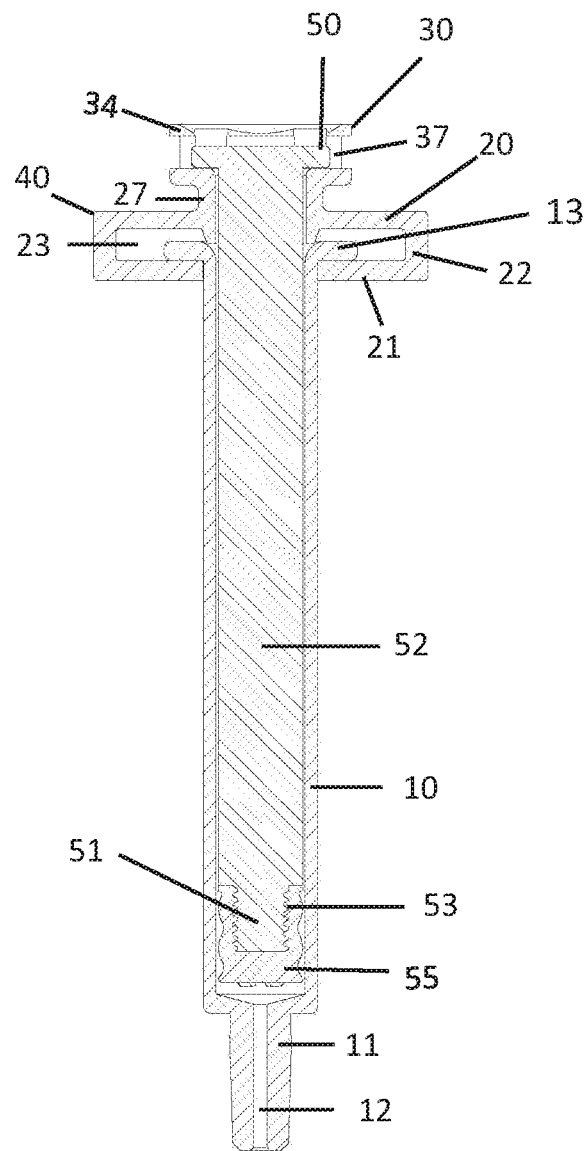

When the plunger rod 5 is pushed further forward towards the distal end 11 of the syringe barrel 10 from the position shown in FIG. 7f, the disc-shaped proximal end 50 starts to slide along the bevels 35 of the locking noses 34, flexing the resilient locking noses 34 outwards, towards the circumferential side-wall 31 of the plunger rod locking portion 30, and/or causing a certain flexing and bending of the disc-shaped proximal end 50 of the plunger rod 5. As shown in FIG. 7g, finally the disc-shaped proximal end 50 of the plunger rod will have slid beyond the front ends of the bevels 35 of the locking noses 34 to be fully accommodated inside the chamber or receiving space 37 formed by the circumferential side-wall 31 of the plunger rod locking portion 30. More specifically, the disc-shaped proximal end 50 of the plunger rod will have slid into the chamber or receiving space 37 formed between the bottom sides 36 of the locking noses 34 and the annular stop surface 32 at the bottom of the plunger rod locking portion 30, so that the resilient locking noses 34 will flex backward into the communication channel 29 to recapture their home position. In the condition shown in FIGS. 7g and 7i, when the disc-shaped proximal end 50 of the plunger rod abuts against the annular stop surface 32 at the bottom of the chamber 37, the plunger 55 will have reached its foremost distal position in the syringe barrel 10, as shown in FIG. 7i.

In this embodiment, the upper rim of the side-wall 31 above the windows 34a may be relatively thin and form a relatively thin resilient circumferential web along the side-wall 31, which will further assist a proper flexing of the locking noses 34 when the disc-shaped proximal end of the plunger rod slides over the locking noses 34.

Figure 8A:
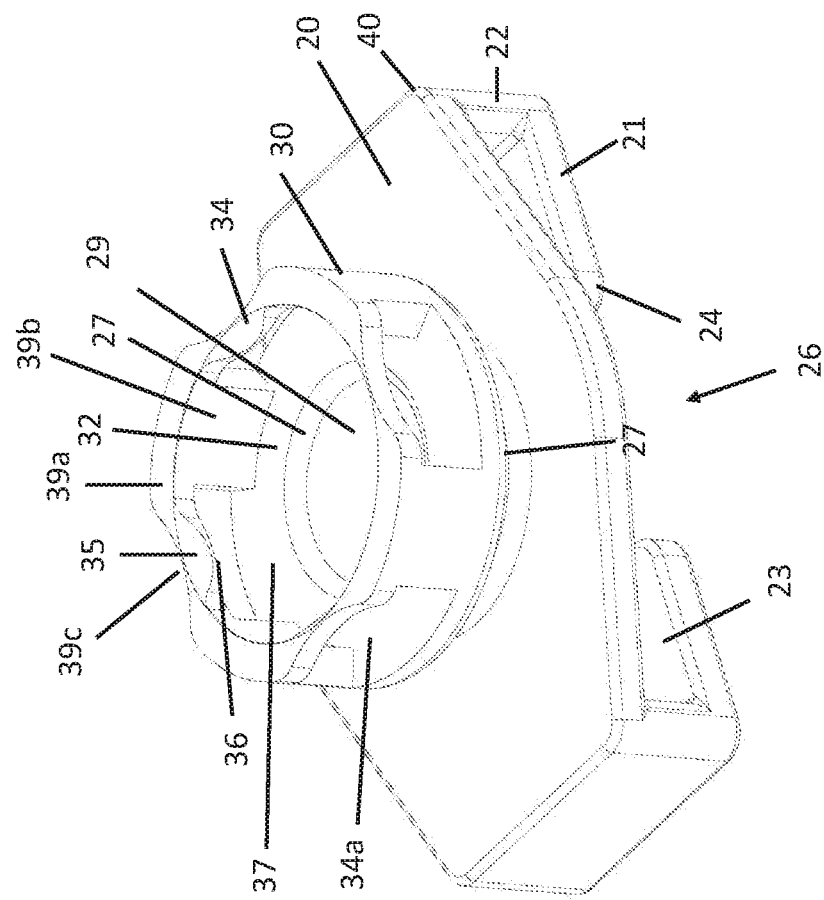
FIG. 8a shows the plunger rod locking device according to a fourth embodiment of the present invention in a perspective view from a front side.
Figure 8C:
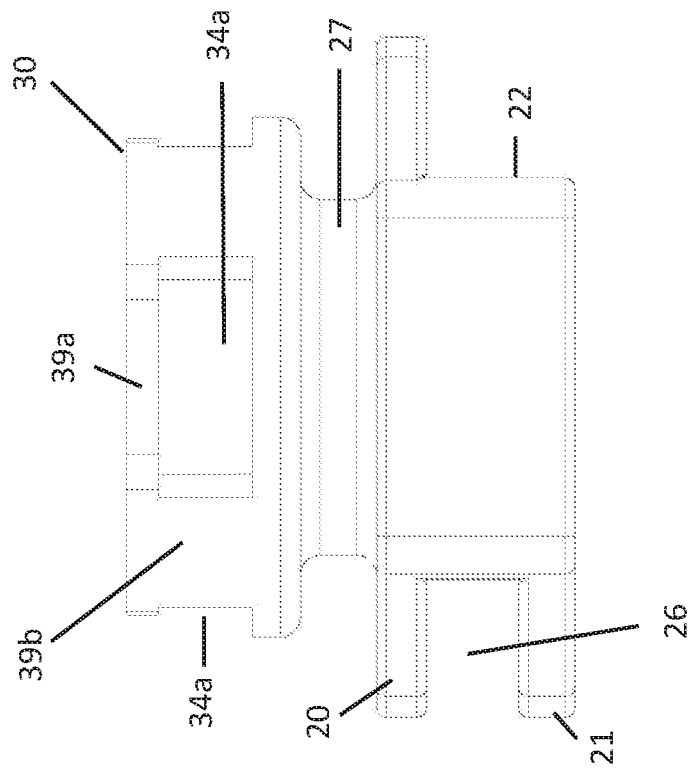
FIGS. 8b and 8c show the plunger rod locking device of FIG. 8a in a top view and in a side view.
Figure 8B:
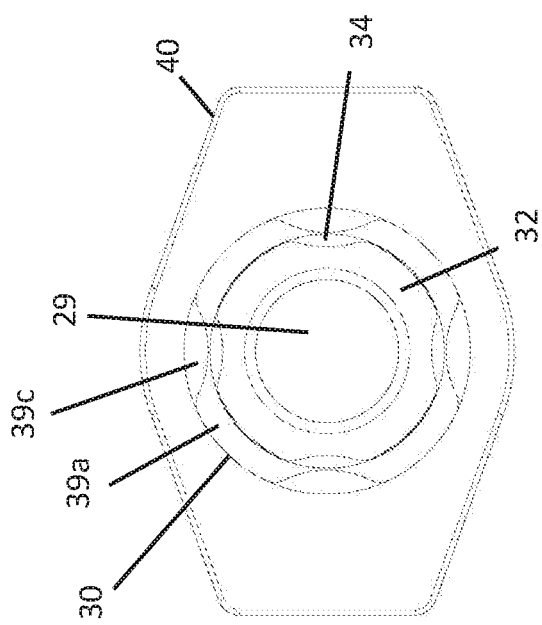

FIGS. 8a to 8c show a further embodiment of the locking device according to the present invention, wherein the chamber 37 of the plunger rod locking portion 30 has an even more open, filigree structure in that the chamber 37 is basically formed by two annular webs, one annular web 39a forming the upper rim of the plunger rod locking portion 30, the annular other web in this example being formed by the annular stop surface 32 at the bottom of the plunger rod locking portion 30. According to another embodiment (not shown), a second annular web similar to the annular web 31 may be provided at the lower end of the chamber 37 and above the annular stop surface 32 at the bottom of the plunger rod locking portion 30.

As shown in FIG. 8a, the upper annular web 39a and the bottom 32 of the plunger rod locking portion 30 are interconnected by a plurality of axial connecting webs 39b that may be relatively thin whereas the windows 34a in-between these axial connecting webs 39b may be relatively wide. It can be said that in this embodiment the chamber or receiving volume 37 of the plunger rod locking portion 30 is formed like a cage with relatively wide windows 34a. Nevertheless, the disc-shaped proximal end of the plunger rod, once locked by the locking noses 34 inside chamber or receiving volume 37 is still sufficiently shielded by the axial connecting webs 39b and the upper annular web 39a to prevent an undesired manipulation of the disc-shaped proximal end of the plunger rod and thereby an inadvertent release of the locking noses 34 so that the disc-shaped proximal end of the plunger rod is reliably locked and retained inside chamber or receiving volume 37 of the plunger rod locking portion 30. For this purpose, the windows 34a may be of a width preventing access to the disc-shaped proximal end of the plunger rod from outside of the chamber or receiving volume 37 or cage e.g. for preventing access for the tip of the little finger of a user to the disc-shaped proximal end of the plunger rod from outside.

As shown in FIG. 8a, locking noses 34 are each formed above a corresponding window 34a on the inner side of the annular web 39a. As shown in the plan view of FIG. 8b, these locking noses 34 may each have a convex front edge protruding into the chamber 37 of the plunger rod locking device 30. At the rear side of each locking nose 34 a convexity 39c may be provided that, on the one hand, may further assist a proper flexing of the annular web 39a when the disc-shaped proximal end of the plunger rod slides over the beveled upper surfaces of the locking noses 34 upon insertion into the chamber 37, and, on the other hand, may further assist a returning force driving the locking noses 34 and the annular web 39a back toward the relaxed home position shown in FIG. 8b once the disc-shaped proximal end of the plunger rod is fully inserted into the chamber or receiving volume 37 of the cage-like structure. Also in this embodiment, the upper surfaces of the locking noses 34 are formed as bevels 35 that are slanted inward and downward under an acute angle toward the chamber or receiving space 37, where the bottom surfaces 36 of the locking noses 34 may extend in parallel to the stop surface 32 at the bottom of the chamber or receiving space 37, to thereby prevent an inadvertent release of the disc-shaped proximal end of the plunger rod once it is locked in the chamber or receiving space 37 formed between the locking noses 34 and the annular bottom 32 of the plunger rod locking portion 30.

For all of the afore-mentioned embodiments, the height of the chamber or receiving volume 37 formed between the bottom sides 36 of the locking noses 34 and the stop surface 32 at the bottom of the plunger rod locking portion 30 in an axial direction of the locking device may be a little larger than the thickness of the disc-shaped proximal end 50 of the plunger rod 5, so that the disc-shaped proximal end 50 is accommodated between the bottom sides 36 of the locking noses 34 and the stop surface 32 at the bottom of the plunger rod locking portion 30 with a certain axial clearance. Thus, the plunger rod 5 is not actually locked without clearance by the plunger rod locking portion 30. Rather, a residual dose of liquid may be injected by further pushing forward the plunger rod 5 toward the distal end 11 of the syringe barrel 10 after the disc-shaped proximal end 50 has slid beyond the locking noses 34, until the disc-shaped proximal end 50 finally abuts against the stop surface 32 at the bottom of the plunger rod locking portion 30, defining the foremost axial position of the plunger 55.

If one compares the sectional views of FIGS. 6a/6b and 7f/7g it becomes clear to the skilled person that a locking device according to the present invention generally may be provided without the afore-mentioned backstop function, that serves for preventing an inadvertent removal or withdrawal of the plunger from the syringe barrel, once the locking device is mounted to the flange at the open proximal end of the syringe barrel. This backstop function is implemented in the embodiment shown in FIGS. 6a and 6b by means of the protrusions 28 narrowing the width of the communication channel 29 to below an outer diameter or width of the plunger (not shown). On the other hand, in the embodiment shown in FIGS. 4f and 7g the protrusions 28 generally do not narrow the communication channel 29 formed in the locking device.

While the disc-shaped proximal end of the plunger rod is shown to be of circular base area in the drawings, it will be appreciated and understood by those skilled in the art that the disc-shaped proximal end of the plunger rod may have a different shape, e.g. a rectangular, quadratic, hexagonal, ovoid or ellipse-shaped shape. While the disc-shaped proximal end of the plunger rod is shown to be formed by bulk material, it will be appreciated and understood by those skilled in the art that the disc-shaped proximal end of the plunger rod may also be partially hollow or interrupted by passages or through-holes or chambers, that may be disposed and configured for assisting a certain flexing and bending of the disc-shaped proximal end of the plunger rod when it slides over the insertion bevels at the upper surfaces of the locking noses of the plunger rod locking device.

While the proximal end of the plunger rod is shown to be disc-shaped in the drawings, it will be appreciated and understood by those skilled in the art that the proximal end of the plunger rod may be of any appropriate shape, as known from the prior art, in which case the at least one positive locking device of the plunger rod locking portion may be of different shape and functionality and may positively engage with other portions at or near the proximal end of the plunger rod in a similar manner as outlined above.

Figure 9:
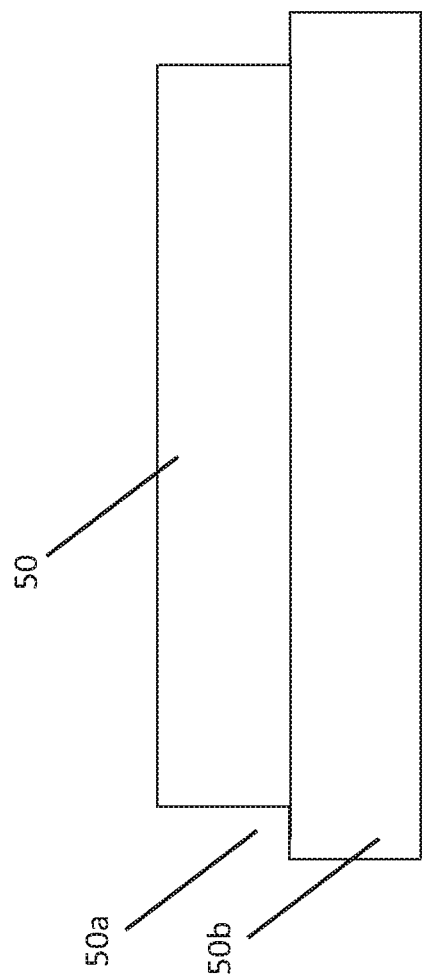
FIG. 9 is a side view of the proximal end of a plunger rod of another embodiment of the present invention.

As shown in FIG. 9, the proximal end 50 of the plunger rod may have an axial step 50a, so that a circumferential radial protrusion 50b is formed at the bottom of the proximal end 50 of the plunger rod that is locked by the at least one locking nose of the plunger rod locking portion, whereas the axial step 50a may extend up to the upper rim of the plunger rod locking portion, which further eases pushing the proximal end 50 of the plunger rod into the plunger rod locking portion in its locked position, and prevents an inadvertent removal of the plunger rod even more reliably.

It will be appreciated and understood by those skilled in the art that the plunger rod locking device with backstop function according to the present invention provides the functionality both of a backstop device for preventing inadvertent removal of a plunger from a syringe and of a tamper-evident plunger rod locking device for locking the plunger rod at the proximal end of the syringe once a dose of medication has been injected by pushing the plunger rod fully forward and for preventing re-use of the syringe. It will be appreciated and understood by those skilled in the art that the plunger rod locking device with backstop function according to the present invention may be integrally formed in any one of conventional manners such as injection molding. It may be formed from appropriate medical grade plastics, hard rubber materials, glass, metals or the like.

It will be appreciated and understood by those skilled in the art that the plunger rod locking device with backstop function according to the present invention can be placed on the syringe flange regardless of the presence or absence of the plunger.

While the preferred embodiments of the present invention have been described so as to enable one skilled in the art to practice the device of the present invention, it is to be understood that variations and modifications may be employed without departing from the concept and intent of the present invention as defined in the appended claims. Accordingly, the preceding description is intended to be exemplary and should not be used to limit the scope of the invention. The scope of the invention should be determined only by reference to the appended claims.

LIST OF REFERENCE NUMERALS

1 syringe
2 plunger rod locking device
3 syringe with plunger rod locking device 2
5 plunger rod
10 cylindrical syringe barrel body
11 distal end
12 injection channel
13 flange/finger rest
14 rounded inner edge of flange 13
15 open proximal end
16 inner volume/chamber
19 liquid
20 top plate
21 bottom plate
22 side wall
23 interspace
24 rounded locking edge
25 semi-circular inner edge
25a leading edge
26 aperture
27 connecting portion
28 locking protrusion
29 communication channel
30 plunger rod locking member
31 cylindrical side wall
32 stop surface
33 proximal edge
34 locking nose
34a window
35 bevel of locking nose 34

36 bottom side of locking nose 34
37 chamber/receiving space
38 clearance
39a annular web
39b axial connecting web
39c convexity
40 mounting device
50 proximal end of plunger rod 5
50a axial step
50b radial protrusion
51 distal end
52 shaft
53 thread
55 plunger

The invention claimed is:

1. A locking device for locking a plunger rod of a syringe after use and preventing re-use of the syringe, wherein
the syringe includes a barrel having an open proximal end and a flange provided adjacent said open proximal end, wherein the barrel is configured to receive the plunger rod through said open proximal end and a proximal end of the plunger rod is formed disc-shaped and the flange is relatively slim in a direction transverse to a longitudinal direction of the barrel,
said locking device comprising
a mounting portion configured for mounting the locking device to the flange adjacent said open proximal end of the barrel by positive-fit by pushing the mounting portion onto the flange along the direction transverse to the longitudinal direction of the barrel and clipping the mounting portion onto the flange, and
a plunger rod locking portion for locking an axial position of the plunger rod after use of the syringe, wherein
an outer width of the mounting portion is larger than an outer width of the flange so that the mounting portion is configured to serve as a finger rest during use of the syringe,
a communication channel is formed in the locking device for enabling insertion of the plunger rod into the open proximal end of the barrel via the plunger rod locking portion and the mounting portion; wherein
a width of the communication channel is larger inside the plunger rod locking portion to form a chamber for receiving the disc-shaped proximal end of the plunger rod after use of the syringe, and
the plunger rod locking portion comprises a plurality of positive locking devices configured to positively lock the axial position of the plunger rod by positive-fit engagement with the disc-shaped proximal end of the plunger rod, for locking the plunger rod at or near a foremost axial position of a distal end of the plunger rod in the barrel after use of the syringe; wherein
the chamber formed by the plunger rod locking portion is configured for preventing full access to the disc-shaped proximal end of the plunger rod from outside the plunger rod locking portion, to prevent withdrawal of the disc-shaped proximal end of the plunger rod out of the chamber, when the axial position of the plunger rod is positively locked,
the plunger rod locking portion is formed as a cage-like cylindrical member formed by two annular webs interconnected by a plurality of axial connecting webs, wherein each positive locking device of the plurality of positive locking devices is provided on an inner side of an annular web or of an axial connecting web, and
a width of the communication channel is reduced at least in sections to a width that is smaller than an outer diameter of a plunger used for sealing the barrel, for preventing inadvertent removal of the plunger from the barrel via the communication channel.

2. The locking device as claimed in claim 1, wherein a stop surface is provided at a bottom of said chamber for defining the foremost axial position of the distal end of the plunger rod in the barrel by abutment of the disc-shaped proximal end of the plunger rod with the stop surface.

3. The locking device as claimed in claim 1, wherein the plurality of positive locking devices is configured to retain the disc-shaped proximal end of the plunger rod inside the chamber and to prevent withdrawal of the disc-shaped proximal end of the plunger rod toward a proximal end of the plunger rod locking portion beyond a minimum distance to a proximal upper rim of the plunger rod locking portion, when the axial position of the plunger rod is positively locked, wherein the minimum distance corresponds at least to an axial length of the at least one positive locking device.

4. The locking device as claimed in claim 1, wherein each positive locking device of the plurality of positive locking devices is formed as a locking nose radially protruding into the plunger rod locking portion and being configured for positive-fit engagement with the disc-shaped proximal end of the plunger rod.

5. The locking device as claimed in claim 4, wherein each locking nose is configured to be resiliently deformed or flexed when the disc-shaped proximal end of the plunger rod is pushed beyond the at least one locking nose before the distal end of the plunger rod reaches its foremost axial position in the barrel.

6. The locking device as claimed in claim 4, wherein each locking nose is formed at a window, which is formed in the plunger rod locking portion such that the chamber communicates with an outside of the plunger rod locking portion.

7. The locking device as claimed in claim 4, wherein the each locking nose has a beveled upper surface facing towards a proximal open end of the plunger rod locking portion and a bottom side extending radially inwards into the chamber formed by the plunger rod locking portion.

8. The locking device as claimed in claim 1, wherein a height of the chamber formed by the plunger rod locking portion in an axial direction of the device is equal to a thickness of the disc-shaped proximal end of the plunger rod; or is larger than a thickness of the disc-shaped proximal end of the plunger rod.

9. The locking device as claimed in claim 1, wherein the mounting portion comprises an upper plate directed towards the proximal end of the communication channel and a bottom plate opposite to said upper plate, an interspace being formed between the upper and bottom plate, wherein at least one protrusion is formed at a proximal end of the mounting portion protruding from the upper plate into the interspace and configured for positive-fit engagement with the open proximal end of the barrel, for mounting the locking device on the flange of the barrel.

10. The locking device as claimed in claim 9, wherein at least a bottom end of the at least one protrusion facing the bottom plate of the mounting portion is resilient.

11. The locking device as claimed in claim 9, wherein the at least one protrusion has a tapered profile having an outer diameter corresponding to the inner diameter of the barrel at the open proximal end, wherein a height of the interspace formed between the upper and bottom plate of the mounting portion preferably corresponds to a height of the flange at the open proximal end of the barrel.

12. The locking device as claimed in claim 1, further comprising at least one protrusion provided in the communication channel reducing the width of the communication channel at least in sections to a width that is smaller than an outer diameter of a plunger used for sealing the barrel, for preventing inadvertent removal of the plunger from the barrel via the communication channel.

13. The locking device as claimed in claim 1, wherein the plurality of axial connecting webs are provided at equidistant spacing along a circumferential direction of the two annular webs, wherein each of the plurality of positive locking devices radially protrudes into the plunger rod locking portion to thereby form a locking structure of an opening width, which is slightly less than a maximum outer width of the disc-shaped proximal end of the plunger rod, wherein each of the plurality of locking noses has a beveled upper surface facing towards a proximal open end of the plunger rod locking portion under an acute angle.

14. A syringe assembly comprising:
a syringe barrel pre-filled with a selected dose of medication and having a distal end, an open proximal end opposite to the distal end, a sidewall extending between the distal end and the open proximal end defining a chamber, and a flange provided adjacent said open proximal end, the flange being relatively slim in a direction transverse to a longitudinal direction of the barrel;
a plunger disposed within the chamber of the syringe barrel;
a plunger rod associated with the plunger and connected with the plunger, a proximal end of the plunger rod being formed disc-shaped; and
a locking device, which is mounted to the flange adjacent said proximal end by positive-fit, for locking the plunger rod at or near a foremost axial position of the distal end of the plunger rod in the barrel after use of the syringe and preventing re-use of the syringe; wherein
said locking device comprises
a mounting portion clipped onto the flange adjacent said open proximal end of the syringe barrel by positive-fit by pushing the mounting portion onto the flange along the direction transverse to the longitudinal direction of the syringe barrel, and
a plunger rod locking portion for locking the axial position of the plunger rod after use of the syringe, wherein
an outer width of the mounting portion is larger than an outer width of the flange so that the mounting portion is configured to serve as a finger rest during use of the syringe,
a communication channel is formed in the locking device for enabling insertion of the plunger rod into the open proximal end of the barrel via the plunger rod locking portion and the mounting portion; wherein
a width of the communication channel is larger inside the plunger rod locking portion to form a chamber for receiving the disc-shaped proximal end of the plunger rod after use of the syringe, and
the plunger rod locking portion comprises a plurality of positive locking devices configured to positively lock the axial position of the plunger rod by positive-fit engagement with the disc-shaped proximal end of the plunger rod, for locking the plunger rod at or near a foremost axial position of a distal end of the plunger rod in the syringe barrel after use of the syringe; wherein
the chamber formed by the plunger rod locking portion is configured for preventing full access to the disc-shaped proximal end of the plunger rod from outside the plunger rod locking portion, to prevent withdrawal of the disc-shaped proximal end of the plunger rod out of the chamber, when the axial position of the plunger rod is positively locked,
the plunger rod locking portion is formed as a cage-like cylindrical member formed by two annular webs interconnected by a plurality of axial connecting webs, wherein each positive locking device of the plurality of positive locking devices is provided on an inner side of an annular web or of an axial connecting web, and
a width of the communication channel is reduced at least in sections to a width that is smaller than an outer diameter of a plunger used for sealing the barrel, for preventing inadvertent removal of the plunger from the barrel via the communication channel.

15. The syringe assembly as claimed in claim 14, wherein each positive locking device is formed as a locking nose radially protruding into the plunger rod locking portion and being configured for positive-fit engagement with the disc-shaped proximal end of the plunger rod.

16. The syringe assembly as claimed in claim 15, wherein each locking nose is configured to be resiliently deformed or flexed when the disc-shaped proximal end of the plunger rod is pushed beyond the at least one locking nose before the distal end of the plunger rod reaches its foremost axial position in the barrel.

17. The syringe assembly as claimed in claim 14, wherein the plurality of axial connecting webs are provided at equidistant spacing along a circumferential direction of the two annular webs, wherein each of the plurality of positive locking devices radially protrudes into the plunger rod locking portion to thereby form a locking structure of an opening width, which is slightly less than a maximum outer width of the disc-shaped proximal end of the plunger rod, wherein each of the plurality of locking noses has a beveled upper surface facing towards a proximal open end of the plunger rod locking portion under an acute angle.

18. A locking device for locking a plunger rod of a syringe after use and preventing re-use of the syringe, wherein
the syringe includes a barrel having an open proximal end and a flange provided adjacent said open proximal end, wherein the barrel is configured to receive the plunger rod through said open proximal end and a proximal end of the plunger rod is formed disc-shaped,
said locking device comprising
a mounting portion configured for mounting the locking device to the flange adjacent said open proximal end of the barrel by positive-fit by pushing the mounting portion onto the flange along the direction transverse to the longitudinal direction of the barrel and clipping the mounting portion onto the flange, and
a plunger rod locking portion for locking an axial position of the plunger rod after use of the syringe, wherein
a communication channel is formed in the locking device for enabling insertion of the plunger rod into the open proximal end of the barrel via the plunger rod locking portion and the mounting portion; wherein
a width of the communication channel is larger inside the plunger rod locking portion to form a chamber for receiving the disc-shaped proximal end of the plunger rod after use of the syringe,
the plunger rod locking portion comprises a plurality of positive locking devices configured to positively lock the axial position of the plunger rod by positive-fit engagement with the disc-shaped proximal end of the plunger rod, for locking the plunger rod at or near a foremost axial position of a distal end of the plunger rod in the barrel after use of the syringe, and the plunger rod locking portion is formed as a cage-like cylindrical member formed by two annular webs interconnected by a plurality of axial connecting webs, wherein each positive locking device of the plurality of positive locking devices is provided on an inner side of an annular web or of an axial connecting web.

\* \* \* \* \*